(12) United States Patent
Okamoto et al.

US009499638B2

(10) Patent No.: US 9,499,638 B2
(45) Date of Patent: Nov. 22, 2016

(54) POLYSACCHARIDE DERIVATIVE AND SEPARATING AGENT FOR OPTICAL ISOMER CONTAINING THE SAME

(71) Applicants: Yoshio Okamoto, Nagoya (JP); Chiyo Yamamoto, Suzuka (JP); Shunsuke Kondo, Nagoya (JP); Masami Kamigaito, Nagoya (JP)

(72) Inventors: Yoshio Okamoto, Nagoya (JP); Chiyo Yamamoto, Suzuka (JP); Shunsuke Kondo, Nagoya (JP); Masami Kamigaito, Nagoya (JP)

(73) Assignee: DAICEL CORPORATION, Osaka-shi, Osaka (JP)

( * ) Notice: Subject to any disclaimer, the term of this patent is extended or adjusted under 35 U.S.C. 154(b) by 53 days.

(21) Appl. No.: 14/067,419

(22) Filed: Oct. 30, 2013

(65) Prior Publication Data

US 2014/0128597 A1 May 8, 2014

Related U.S. Application Data

(62) Division of application No. 12/310,706, filed as application No. PCT/JP2007/067175 on Sep. 4, 2007, now abandoned.

(30) Foreign Application Priority Data

Sep. 4, 2006 (JP) ................................. 2006-239444
May 7, 2007 (JP) ................................. 2007-122606

(51) Int. Cl.
| | |
|---|---|
| *C08B 15/00* | (2006.01) |
| *C08B 15/06* | (2006.01) |
| *C08B 33/02* | (2006.01) |
| *B01J 20/26* | (2006.01) |
| *B01J 20/285* | (2006.01) |
| *B01J 20/286* | (2006.01) |
| *B01J 20/29* | (2006.01) |
| *B01J 20/32* | (2006.01) |
| *C07B 57/00* | (2006.01) |
| *C08B 33/00* | (2006.01) |
| *C08B 33/04* | (2006.01) |
| *C08B 33/06* | (2006.01) |

(52) U.S. Cl.
CPC .............. *C08B 33/02* (2013.01); *B01J 20/262* (2013.01); *B01J 20/265* (2013.01); *B01J 20/285* (2013.01); *B01J 20/286* (2013.01); *B01J 20/29* (2013.01); *B01J 20/328* (2013.01); *B01J 20/3272* (2013.01); *C07B 57/00* (2013.01); *C08B 33/00* (2013.01); *C08B 33/04* (2013.01); *C08B 33/06* (2013.01)

(58) Field of Classification Search
CPC ........ C08B 15/00; C08B 15/06; C08B 33/02
USPC ......... 536/55.3, 124, 18.7, 20, 30, 45, 123.1
See application file for complete search history.

(56) References Cited

U.S. PATENT DOCUMENTS

| | | | |
|---|---|---|---|
| 3,376,286 A | 4/1968 | Germino et al. | |
| 4,818,394 A | 4/1989 | Okamoto et al. | |
| 4,997,935 A | 3/1991 | Diamantoglou | |
| 5,191,072 A * | 3/1993 | Hasegawa et al. | ........... 536/117 |
| 5,491,223 A | 2/1996 | Okamoto | |
| 5,543,506 A | 8/1996 | Okamoto | |
| 5,639,824 A | 6/1997 | Okamoto | |
| 5,663,311 A | 9/1997 | Okamoto | |
| 6,379,552 B1 | 4/2002 | Kitagawa et al. | |
| 7,745,616 B2 | 6/2010 | Okamoto et al. | |
| 2003/0162745 A1 | 8/2003 | Klohr et al. | |

FOREIGN PATENT DOCUMENTS

| | | |
|---|---|---|
| EP | 0 157 365 A2 | 10/1985 |
| EP | 2 028 487 A1 | 2/2009 |
| EP | 2 031 388 A1 | 3/2009 |
| EP | 2 113 769 A1 | 11/2009 |
| JP | 5-163164 A | 6/1993 |
| JP | 11-349494 | 12/1999 |
| JP | 11349494 A * | 12/1999 |
| JP | 2000-253894 | 9/2000 |
| JP | 2000-290201 | 10/2000 |
| JP | 3272354 B2 | 1/2002 |
| WO | WO 92/15616 | 9/1992 |
| WO | WO 92/15617 | 9/1992 |
| WO | WO 2007/129658 | 11/2007 |
| WO | WO 2007/129659 | 11/2007 |
| WO | WO 2008/102920 | 8/2008 |

OTHER PUBLICATIONS

European Search Report dated Sep. 12, 2011 (12 pages).
"Synthesis of Natural- and Non-natural-type Aminopolysaccharides: 2-Acetamido-2-deoxy-β-D-glucopyranan Derivatives by Acid-Catalyzed Polymerization of 2-Methyl(3,6- and 3,4-di-O-benzyl-1,2-dideoxy-α-D-glucopyrano)-[2,1[*d*]-2-oxazolines Involving Stereoregular Glycosylation" by J. Kadokawa et al, Macromolecules, American Chemical Society, vol. 30, No. 26, Dec. 1997, pp. 8212-8217.
"Mixed Esters of Amylose" by Ivan Wolff et al, Industrial & Engineering Chemistry, vol. 49, No. 8, Aug. 1957, pp. 1247-1248.
"Analysis of Side Group Motion in *O*-acetyl-starch using Regioselective 2-*O*-acetyl-starches by Means of Dielectric Spectroscopy" by J. Einfeldt et al, Polymer, Elsevier Science Publishers B.V., vol. 41, No. 26, Dec. 2000, pp. 9273-9281.

(Continued)

*Primary Examiner* — Sudhakar Katakam
*Assistant Examiner* — Everett White
(74) *Attorney, Agent, or Firm* — Flynn, Thiel, Boutell & Tanis, P.C.

(57) ABSTRACT

The present invention provides: a polysaccharide derivative containing a structure wherein hydrogen atoms in a hydroxyl group at the 2-position and the 3-position of a structure unit of polysaccharide are substituted with different substituents respectively represented by a specific general formula and a separating agent for optical isomers which contains such a polysaccharide derivative. The present invention can provide a novel polysaccharide derivative which has excellent optical isomer separating ability, making it suitable as a separating agent for optical isomers, and can provide a separating agent for optical isomers which contains the polysaccharide derivative.

7 Claims, 18 Drawing Sheets

(56) References Cited

OTHER PUBLICATIONS

"Cyclodextrin Carbamates as Novel Chiral Stationary Phases for Capillary Gas Chromatography" by Tsutomu Takeichi et al, Journal of High Resolution Chromatography, vol. 18, No. 3, Mar. 1995, pp. 179-189.

"Characterization of Cyclomalto-Hexaose and -Heptaose Derivatives by the Reductive-Cleavage Method" by Petra Mischnick-Lubbecke et al, Carbohydrate Research, vol. 187, No. 2, Apr. 1989, pp. 197-202.

"Multichromophoric Cyclodextrins. 1. Synethesis of O-Naphthoyl-β-cyclodextrins and Investigation of Excimer Formation and Energy Hopping" by Mario Berberan-Santos et al, Journal of the American Chemical Society, vol. 114, No. 16, Jul. 1992, pp. 6427-6436.

Synthesis of Natural- and Non-natural-type Aminopolysaccharides: 2-Acetamido-2-deoxy-β-D-glucopyranan Derivatives by Acid-Catalyzed Polymerization of 2-Methyl(3,6- and 3,4-di-O-benzyl-1,2-dideoxy-α-D-glucopyrano)-p2,1-$d$]-2-oxazolines Involving Stereoregular Glycosylation, by J. Kadokawa et al, Macromolecules, 1997, 30(26), pp. 8212-8217.

Cyclodextrin carbamates as novel chiral stationary phases for capillar gas chromatography, by T. Takeichi et al, Journal of High Resolution Chromatography, Mar. 1995, vol. 18, Issue 3, pp. 179-189.

Characterization of cyclomalto-hexaose and -heptaose derivatives by the reductive-cleavage method, by P. Mischnick-Lübbecke, Carbohydrate Research, 1989, vol. 187, pp. 197-202.

Analysis of side group motion in O-acetyl-starch using regioselective 2-O-acetyl-starches by means of dielectric spectroscopy, by J. Einfeldt et al, Polymer, 2000, vol. 41, pp. 9273-9281.

"A straight way to regioselectively functionalized polysaccharide esters" by René Dicke, Cellulose 11: 255-263, (2004).

"4-Methoxy substituted trityl groups in 6-O protection of cellulose: Homogeneous synthesis, characterization, detritylation" by Juan A. Camacho Gómez, Ulrich W. Erler, Dieter O. Klemm, Macromol. Chem. Phys. 197, 953-964 (1996).

\* cited by examiner

POLYSACCHARIDE DERIVATIVE AND SEPARATING AGENT FOR OPTICAL ISOMER CONTAINING THE SAME

This is a division of Ser. No. 12/310,706, filed Mar. 3, 2009, which was the national stage of International Application No. PCT/JP2007/067175, filed Sep. 4, 2007, which International Application was not published in English.

TECHNICAL FIELD

The present invention relates to a polysaccharide derivative useful in separating optical isomers, and a separating agent for optical isomers containing the polysaccharide derivative.

BACKGROUND ART

A polysaccharide derivative obtained by modifying the hydroxyl groups or amino groups of a polysaccharide with various substituents is known to serve as a chiral stationary phase in chromatography to show a high optical resolution, and a large number of kinds of polysaccharide derivatives have been heretofore synthesized.

Examples of such polysaccharide derivative useful as a separating agent for optical isomers include: an ester derivative of a polysaccharide (see, for example, Patent Document 1); an alkyl-substituted phenylcarbamate of a polysaccharide except cellulose (see, for example, Patent Document 2); a chitosan derivative (see, for example, Patent Document 3); a cyclodextrin derivative (see, for example, Patent Document 4); a polysaccharide derivative obtained by substituting the hydroxyl groups or amino groups of a polysaccharide with two or more kinds of different substituents (see, for example, Patent Document 5); a polysaccharide derivative obtained by specifically introducing a substituent into the 2-position of a polysaccharide (see, for example, Non-patent Document 1); and a polysaccharide derivative obtained by specifically introducing a substituent into the 6-position of a polysaccharide by the protection of a hydroxyl group at the 6-position by a trityl group and deprotection (see, for example, Non-patent Document 2).

However, a polysaccharide derivative having a specific kind of a substituent at a specific position, in particular a polysaccharide derivative having specific substituents different from each other at its 2- and 3-positions that are hard to distinguish in the introduction of a substituent into a hexose leaves room for future studies.

Patent Document 1: JP 1466384 B
Patent Document 2: JP 1799654 B
Patent Document 3: JP 3041116 B
Patent Document 4: JP 3342482 B
Patent Document 5: JP 3272354 B
Non-Patent Document 1: Cellulose 11: 255-263, 2004
Non-Patent Document 2: Macromol. Chem. Phys. 1996, 197, 953

DISCLOSURE OF THE INVENTION

The present invention provides a novel polysaccharide derivative excellent in optical isomer separating ability and suitable for a separating agent for optical isomers, and a separating agent for optical isomers containing the polysaccharide derivative.

The present invention provides a polysaccharide derivative having different kinds of substituents introduced into its 2- and 3-positions. In particular, the present invention provides a polysaccharide derivative obtained by substituting hydroxyl groups or amino groups at the 3- and 6-positions of a polysaccharide with substituents of one kind different from that at a 2-position of the polysaccharide, a polysaccharide derivative obtained by randomly substituting hydroxyl groups or amino groups at the 3- and 6-positions of a polysaccharide with substituents of two kinds different from that at a 2-position of the polysaccharide, and a polysaccharide derivative obtained by substituting hydroxyl groups or amino groups at the 3- and 6-positions of a polysaccharide with substituents of two kinds different from that at a 2-position of the polysaccharide. Further, the present invention provides, as a method of producing any such polysaccharide derivative, a method involving: specifically introducing a substituent into only a hydroxyl group or amino group at a 2-position of a polysaccharide; and introducing a substituent different from the substituent at the 2-position into at least a 3-position of the polysaccharide. Further, the present invention provides a method involving: specifically introducing a substituent into a hydroxyl group or amino group at the 2-position of a hexose; protecting a hydroxyl group or amino group at the 6-position of the hexose after the introduction; introducing a substituent different from the substituent at the 2-position into a hydroxyl group or amino group at the 3-position of the hexose; deprotecting the 6-position; and specifically introducing a substituent into the 6-position.

In addition, the present invention provides, as the method of producing the polysaccharide derivative, a method involving: protecting a hydroxyl group or amino group at a 2-position of a polysaccharide; introducing a specific substituent into at least a 3-position of the polysaccharide; deprotecting the 2-position after the introduction; and introducing another specific substituent into the 2-position. Further, the present invention provides a method involving: protecting a hydroxyl group or amino group at the 2-position of a hexose; introducing a specific substituent into each of the 3- and 6-positions of the hexose; and introducing another specific substituent into the 2-position when deprotecting only the 2-position, or introducing another specific substituent into each of the 2- and 6-positions when deprotecting the 2-position and demodifying the 6-position.

In addition, the present invention provides, as the method of producing the polysaccharide derivative, a method involving: protecting a hydroxyl group or amino group at the 2-position of a hexose; protecting a hydroxyl group or amino group at the 6-position of the hexose after the protection; introducing a specific substituent into a hydroxyl group or amino group at the 3-position of the hexose; deprotecting the 6-position; introducing a specific substituent different from that at the 3-position into the 6-position; deprotecting the 2-position; and introducing a specific substituent different from those at the 3- and 6-positions into the 2-position.

That is, the present invention provides a polysaccharide derivative including a structure in which hydrogen atoms of at least hydroxyl groups or amino groups at 2- and 3-positions out of hydroxyl groups or amino groups of structural units of a polysaccharide are substituted with different substituents each represented by any one of the following general formulae (I) to (III):

—CO—R      (I)

—CO—NH—R      (II)

—R      (III)

where R represents an aliphatic or aromatic hydrocarbon group which may contain a heteroatom, and the group may further have a substituent.

In addition, the present invention further provides the polysaccharide derivative which includes a structure in which the hydrogen atoms of the hydroxyl groups or amino groups at the 2-positions in the structural units are each substituted with a substituent represented by the general formula (I).

In addition, the present invention further provides the polysaccharide derivative which includes a structure in which the hydrogen atoms of the hydroxyl groups or amino groups at the 2-positions in the structural units are each substituted with a substituent represented by the general formula (II).

In addition, the present invention further provides the polysaccharide derivative which includes a structure in which the hydrogen atoms of the hydroxyl groups or amino groups at the 3-positions in the structural units are each substituted with a substituent represented by the general formula (II).

In addition, the present invention further provides the polysaccharide derivative in which: the structural units each are a hexose further having a hydroxyl group or amino group at its 6-position; and the polysaccharide derivative further includes a structure in which a hydrogen atom of the hydroxyl group or amino group at the 6-position in each of the structural units is substituted with a substituent represented by any one of the general formulae (I) to (III).

In addition, the present invention further provides each of the polysaccharide derivative which includes a structure in which hydrogen atoms of the hydroxyl groups or amino groups at the 3- and 6-positions in the structural units are substituted with two kinds of substituents each represented by the general formula (II); the polysaccharide derivative which includes a structure in which hydrogen atoms of the hydroxyl groups or amino groups at the 3- and 6-positions in the structural units are each substituted with one kind of substituent represented by the general formula (II); the polysaccharide derivative which includes a structure in which hydrogen atoms of the hydroxyl groups or amino groups at the 3- and 6-positions in the structural units are irregularly substituted with two or more kinds of substituents each represented by the general formula (II); the polysaccharide derivative which includes a structure in which hydrogen atoms of the hydroxyl groups or amino groups at the 1- and 6-positions in the structural units are each substituted with one kind of substituent each represented by the general formula (II); and the polysaccharide derivative which includes a structure in which hydrogen atoms of the hydroxyl groups or amino groups at the 2- and 6-positions in the structural units are substituted with two kinds of substituents represented by the general formula (II).

In addition, the present invention further provides the polysaccharide derivative which includes amylose as the polysaccharide.

In addition, the present invention provides a first method of producing a polysaccharide derivative including the steps of: modifying a hydroxyl group or amino group at a 2-position of each of structural units of a polysaccharide with a first substituent represented by any one of the general formulae (I) to (III); and modifying a hydroxyl group or amino group at a 3-position of the structural unit with a second substituent represented by any one of the general formulae (I) to (III) and different from the first substituent.

In addition, the present invention further provides the first method in which the first substituent is a substituent represented by the general formula (I).

In addition, the present invention further provides the first method in which: the structural units each are a hexose further having a hydroxyl group or amino group at its 6-position; and the method further includes the step of protecting the hydroxyl group or amino group at the 6-position with a protective group after modifying the hydroxyl group or amino group at the 2-position.

In addition, the present invention further provides the first method, further including the steps of: removing the protective group at the 6-position after modifying the hydroxyl group or amino group at the 3-position; and modifying the hydroxyl group or amino group at the 6-position from which the protective group has been removed with a third substituent represented by any one of the general formulae (I) to (III) and different from the second substituent.

In addition, the present invention provides a second method of producing a polysaccharide derivative, including: a 2-position protecting step of protecting a hydroxyl group or amino group at a 2-position of each of structural units of a polysaccharide with a protective group; a 3-position modifying step of modifying a hydroxyl group or amino group at a 3-position of the structural unit the 2-position of which has been protected with a second substituent represented by any one of the general formulae (I) to (III); a 2-position deprotecting step of removing the protective group at the 2-position in the structural unit the 3-position of which has been modified; and a 2-position modifying step of modifying the hydroxyl group or amino group at the 2-position from which the protective group has been removed with a first substituent represented by the same general formula as the general formula of the second substituent but different from the second substituent.

In addition, the present invention further provides the second method in which: the structural units each are a hexose further having a hydroxyl group or amino group at its 6-position; and the 3-position modifying step is a step of modifying each of the hydroxyl groups or amino groups at both the 3- and 6-positions of the structural units with the second substituent.

In addition, the present invention further provides the second method in which: the 2-position deprotecting step is a step of removing both the protective group at the 2-position and the second substituent at the 6-position; and the 2-position modifying step is a step of modifying each of the hydroxyl groups or amino groups at both the 2- and 6-positions of the structural units with the first substituent.

In addition, the present invention further provides the second method in which the first and second substituents each are a substituent represented by the general formula (II).

In addition, the present invention further provides the second method in which: the structural units each are a hexose further having a hydroxyl group or amino group at its 6-position; the method further includes a 6-position protecting step of protecting the hydroxyl group or amino group at the 6-position of the structural unit the 2-position of which has been protected with a protective group before the 3-position modifying step, a 6-position deprotecting step of deprotecting the protective group at the 6-position in the structural unit the 3-position of which has been modified in the 3-position modifying step before the 2-position deprotecting step, and a 6-position modifying step of modifying the hydroxyl group or amino group at the 6-position from which the protective group has been removed with a third substituent represented by the same general formula as the general formula of each of the first and second substituents but different from the first and second substituents; and the 2-position deprotecting step is a step of removing the protective group at the 2-position in the structural unit the 6-position of which has been modified.

In addition, the present invention further provides the second method in which the first, second, and third substituents each are a substituent represented by the general formula (II).

In addition, the present invention provides a separating agent for optical isomers, including the polysaccharide derivative.

The present invention provides a polysaccharide derivative having, at the 2- and 3-positions of a polysaccharide, substituents different from each other and each obtained by substituting a hydrogen atom of a hydroxyl group or amino group with a substituent represented by any one of the general formulae (I) to (III). Accordingly, there can be provided a polysaccharide derivative excellent in optical isomer separating ability and suitable for a separating agent for optical isomers.

In addition, the present invention is additionally effective from the viewpoint of the provision of a polysaccharide derivative excellent in optical isomer separating ability and suitable for a separating agent for optical isomers when the polysaccharide derivative includes a structure in which the hydrogen atoms of the hydroxyl groups or amino groups at the 2-positions in the structural units are each substituted with a substituent represented by the general formula (I).

In addition, the present invention is additionally effective from the viewpoint of the provision of a polysaccharide derivative excellent in optical isomer separating ability and suitable for a separating agent for optical isomers when the polysaccharide derivative includes a structure in which the hydrogen atoms of the hydroxyl groups or amino groups at the 3-positions in the structural units are each substituted with a substituent represented by the general formula (II).

In addition, the present invention is additionally effective from the viewpoint of the provision of a polysaccharide derivative excellent in optical isomer separating ability and suitable for a separating agent for optical isomers when the polysaccharide derivative includes a structure in which the hydrogen atoms of the hydroxyl groups or amino groups at the 2-positions in the structural units are each substituted with a substituent represented by the general formula (II).

In addition, the present invention is additionally effective from the viewpoint of the provision of a polysaccharide derivative excellent in optical isomer separating ability and suitable for a separating agent for optical isomers when the structural units are each a hexose, and the polysaccharide derivative further includes a structure in which a hydrogen atom of the hydroxyl group or amino group at the 6-position of each of the structural units is substituted with a substituent represented by any one of the general formulae (I) to (III).

In addition, the present invention is additionally effective from the viewpoint of the provision of a polysaccharide derivative excellent in optical isomer separating ability for a certain racemic body as an object to be optically resolved and suitable for a separating agent for optical isomers when the polysaccharide derivative has two kinds of substituents each represented by the general formula (II) at, or one kind of a substituent represented by the general formula (II) at each of, the 3- and 6-positions, irregularly has two or more kinds of substituents each represented by the general formula (II) at the 3- and 6-positions, has one kind of a substituent represented by the general formula (II) at each of the 2- and 6-positions, or has two kinds of substituents each represented by the general formula (II) at the 2- and 6-positions.

In addition, the present invention is additionally effective from the viewpoint of the provision of a polysaccharide derivative excellent in optical isomer separating ability and suitable for a separating agent for optical isomers when the polysaccharide is amylose.

In addition, the present invention provides a method including the steps of: modifying a hydroxyl group or amino group at the 2-position of each of the structural units of a polysaccharide with a first substituent represented by any one of the general formulae (I) to (III); and modifying a hydroxyl group or amino group at the 3-position of the structural unit with a second substituent represented by any one of the general formulae (I) to (III) and different from the first substituent. Accordingly, there can be provided a polysaccharide derivative excellent in optical isomer separating ability and suitable for a separating agent for optical isomers.

In addition, the present invention is additionally effective from the viewpoint of the provision of a polysaccharide derivative excellent in optical isomer separating ability and suitable for a separating agent for optical isomers when the first substituent is a substituent represented by the general formula (I).

In addition, the present invention is additionally effective from the viewpoint of the provision of a polysaccharide derivative excellent in optical isomer separating ability and suitable for a separating agent for optical isomers when the structural units are each a hexose further having a hydroxyl group or amino group at its 6-position, and the method further includes the step of protecting the hydroxyl group or amino group at the 6-position with a protective group after the modification of the hydroxyl group or amino group at the 2-position.

In addition, the present invention is additionally effective from the viewpoint of the provision of a polysaccharide derivative excellent in optical isomer separating ability and suitable for a separating agent for optical isomers when the method further includes the steps of: removing the protective group at the 6-position after the modification of the hydroxyl group or amino group at the 3-position; and modifying the hydroxyl group or amino group at the 6-position from which the protective group has been removed with a third substituent represented by any one of the general formulae (I) to (III) and different from the second substituent.

In addition, the present invention provides a method including: a 2-position protecting step of protecting a hydroxyl group or amino group at the 2-position of each of the structural units of a polysaccharide with a protective group; a 3-position modifying step of modifying a hydroxyl group or amino group at the 3-position of the structural unit the 2-position of which has been protected with a second substituent represented by any one of the general formulae (I) to (III); a 2-position deprotecting step of removing the protective group at the 2-position in the structural unit the 3-position of which has been modified; and a 2-position modifying step of modifying the hydroxyl group or amino group at the 2-position from which the protective group has been removed with a first substituent represented by the same general formula as that of the second substituent but different from the second substituent. Accordingly, there can be provided a polysaccharide derivative excellent in ability to separate optical isomers each having a structure in which it is difficult to introduce substituents at 2- and 3-positions accurately, and suitable for a separating agent for optical isomers.

In addition, the present invention is additionally effective from the viewpoint of the provision of the above-mentioned polysaccharide derivative when the structural units each are a hexose further having a hydroxyl group or amino group at its 6-position and the 3-position modifying step is a step of modifying each of the hydroxyl groups or amino groups at both the 3- and 6-positions of the structural units with the second substituent.

In addition, the present invention is additionally effective from the viewpoint of the provision of the above-mentioned polysaccharide derivative when the 2-position deprotecting step is a step of removing both the protective group at the 2-position and the second substituent at the 6-position and the 2-position modifying step is a step of modifying each of the hydroxyl groups or amino groups at both the 2- and 6-positions of the structural units with the first substituent.

In addition, the present invention is additionally effective from the viewpoint of the provision of the above-mentioned polysaccharide derivative when the first and second substituents each are a substituent represented by the general formula (II).

In addition, the present invention is additionally effective from the viewpoint of the provision of a polysaccharide derivative obtained by introducing different substituents into the 2-, 3-, and 6-positions of a hexose, excellent in optical isomer separating ability, and suitable for a separating agent for optical isomers when the structural units are each a hexose further having a hydroxyl group or amino group at its 6-position, the method further includes, between the 2-position protecting step and the 3-position modifying step, a 6-position protecting step of protecting the hydroxyl group or amino group at the 6-position of the structural unit the 2-position of which has been protected with a protective group before the 3-position modifying step, and further includes, between the 3-position modifying step and the 2-position deprotecting step, a 6-position deprotecting step of deprotecting the protective group at the 6-position in the structural unit the 3-position of which has been modified before the 2-position deprotecting step and a 6-position modifying step of modifying the hydroxyl group or amino group at the 6-position from which the protective group has been removed with a third substituent represented by the same general formula as that of each of the first and second substituents but different from the first and second substituents, and the 2-position deprotecting step is a step of removing the protective group at the 2-position in the structural unit the 6-position of which has been modified.

In addition, the present invention is additionally effective from the viewpoint of the provision of the above-mentioned polysaccharide derivative when the first, second, and third substituents each are a substituent represented by the general formula (II).

In addition, the present invention provides a separating agent for optical isomers containing the polysaccharide derivative. Accordingly, there can be provided a separating agent for optical isomers containing a polysaccharide derivative excellent in optical isomer separating ability and suitable for a separating agent for optical isomers.

BEST MODE FOR CARRYING OUT THE INVENTION

Figure 1:
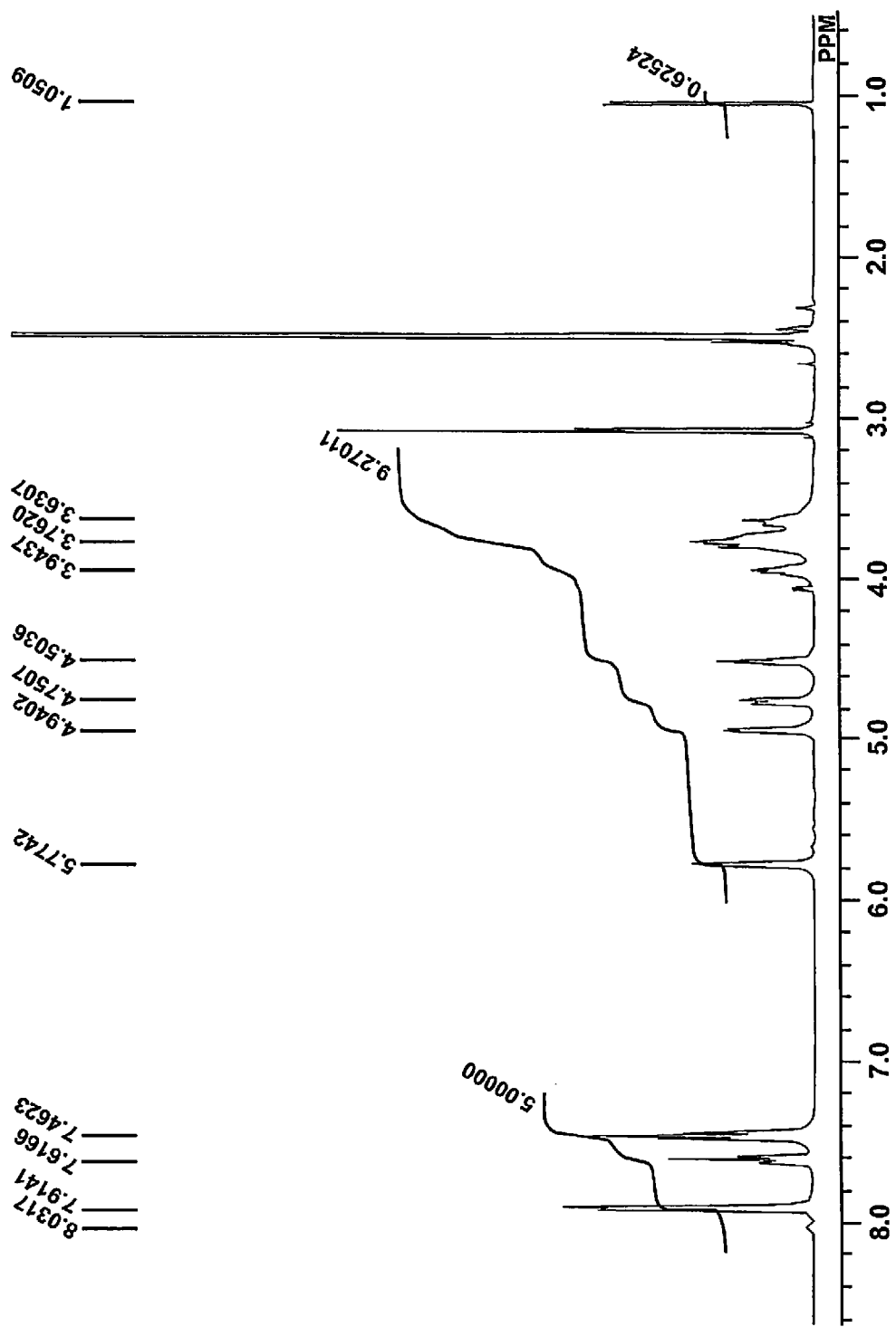
FIG. 1 is a view showing the $^1$H NMR spectrum of Intermediate Product 1-1 obtained in Synthesis Example 1.

A polysaccharide derivative of the present invention includes a structure in which carbon atoms at the 2- and 3-positions of a polysaccharide have substituents different from each other. Further, the polysaccharide derivative includes a structure in which a hydrogen atom of a hydroxyl group or amino group in each of structural units of the polysaccharide is substituted with a substituent represented by any one of the following general formulae (I) to (III). The polysaccharide derivative may be constituted only of the structure, or may further include any other structure.

—CO—R (I)

—CO—NH—R (II)

—R (III)

In the following general formulae (I) to (III), R represents an aliphatic or aromatic hydrocarbon group which may contain a heteroatom, and the group may further have a substituent.

The polysaccharide is not particularly limited so long as it is a polysaccharide having a hydrogen group or amino group at least at the 2- or 3-position. Examples of the polysaccharide include β-1,4-glucan (cellulose), α-1,4-glucan (amylose, amylopectin), α-1,6-glucan (dextran), β-1,6-glucan (pustulan), β-1,3-glucan (cardran, schizophyllan), α-1,3-glucan, β-1,2-glucan (Crown Gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, β-1,4-N-acetylchitosan (chitin), pullulan, agarose, alginic acid, α-cyclodextrin, β-cyclodextrin, γ-cyclodextrin, nigelan, and starches each containing amylose.

Of those, preferred are amylose, β-1,4-chitosan, chitin, β-1,4-mannan, β-1,4-xylan, inulin, cardran, pullulan, α-cyclodextrin, β-cyclodextrin, γ-cyclodextrin, and nigelan. More preferred are amylose, pullulan, and nigelan.

A number average polymerization degree of the polysaccharide (average number of the pyranose or furanose ring contained in one molecule) is preferably 5 or more, and more preferably 10 or more. There is no particular upper limitation, the number average molecular degree is preferably 1,000 or less from a viewpoint of easy handling, more preferably 5 to 1,000, still more preferably 10 to 1,000, and particularly preferably 10 to 500.

The polysaccharide derivative of the present invention includes a structure in which the hydroxyl groups or amino groups of the structural units are modified with one or two or more kinds of substituents each represented by the following general formulae (I) to (III).

   (I)

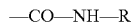   (II)

   (III)

It should be noted that R's in the general formulae (I) to (III) each independently represent an aliphatic or aromatic hydrocarbon group which may contain a heteroatom, and the group may further have a substituent. As the aliphatic hydrocarbon group, a linear or branched aliphatic hydrocarbon group having 1 to 30 carbon atoms is exemplified. Examples thereof include methyl, ethyl, propyl, isopropyl, butyl, tert-butyl, pentyl, octyl, dodecyl, octadecyl, adamantyl, and norbornyl. In addition, as the aromatic hydrocarbon group, an aromatic hydrocarbon group having 6 to 30 carbon atoms and a fused ring is exemplified. Examples thereof include phenyl, indenyl, naphthyl, anthryl, phenanthryl, fluorenyl, pyrenyl, biphenyl, and terphenyl.

As the substituent that R may has, there are exemplified one or two or more substituents selected from the group consisting of a hydrocarbon that has 1 to 12 carbon atoms and may have a heteroatom, cyano, halogen, hydroxyl, nitro, amino, and di (alkyl having 1 to 8 carbon atoms) amino group (i.e. an amino group having an alkyl group having 1 to 8 carbon atoms as a substituent).

All the hydroxyl groups or amino groups at the corresponding positions in the structural units may not be substituted with the substituents each represented by any one of the general formulae (I) to (III) so long as an optical resolution by these substituents can be obtained. The ratio at which the substituents each represented by any one of the general formulae (I) to (III) are introduced into the polysaccharide derivative of the present invention is preferably 70 to 100%, more preferably 80 to 100%, or particularly preferably 100%.

It should be noted that the introduction ratio (%) is defined as described below. That is, the ratio is a ratio of the total number of substituents each represented by any one of the general formulae in the polysaccharide derivative of the present invention to the total number of hydroxyl groups or amino groups of the structural units when the hydroxyl groups or amino groups in the structural units are substituted with the substituents each represented by any one of the general formulae in the polysaccharide derivative of the present invention. The introduction ratio can be determined by utilizing a known analysis method such as NMR or elemental analysis by which one or both of the kind and bonding position of a substituent can be identified. In addition, the introduction ratio can be determined in accordance with the kind of a substituent or the bonding position of the substituent.

For example, when only the hydroxyl groups in the polysaccharide derivative of the present invention are substituted with the substituents each represented by any one of the general formulae (I) to (III), the introduction ratio is a numerical value obtained by multiplying a ratio of the number of substituents each represented by any one of the general formulae to the total number of hydroxyl groups of the polysaccharide after the substitution by 100. When only the amino groups in the polysaccharide derivative are substituted with the substituents each represented by anyone of the general formulae (I) to (III), the introduction ratio is a numerical value obtained by multiplying a ratio of the number of substituents each represented by any one of the general formulae to the total number of amino groups of the polysaccharide after the substitution by 100. When the hydroxyl groups and amino groups in the polysaccharide derivative are substituted with the substituents each represented by any one of the general formulae (I) to (III), the introduction ratio is a numerical value obtained by multiplying a ratio of the total number of substituents each represented by any one of the general formulae to the sum of the total numbers of hydroxyl groups and amino groups of the polysaccharide after the substitution by 100.

In the present invention, the substituent at the 2-position in each of the structural units has only to be a substituent obtained by substituting a hydrogen atom of the hydroxyl group or amino group at the 2-position in the structural unit with a substituent represented by any one of the general formulae (I) to (III); the substituent is preferably a substituent obtained by substituting the hydrogen atom with a substituent represented by the general formula (I) or (II). The substituent represented by the general formula (I) is preferably a benzoyl group. The substituent represented by the general formula (II) is preferably a phenylcarbamoyl group, more preferably a dichlorophenylcarbamoyl group or a dimethylphenylcarbamoyl group, or still more preferably a 3,5-dichlorophenylcarbamoyl group or a 3,5-dimethylphenylcarbamoyl group.

In the present invention, the substituent at the 3-position in each of the structural units is different from the substituent at the 2-position. The substituent at the 3-position in each of the structural units may be a substituent represented by the general formula (I) so long as the substituent is different from the substituent at the 2-position; the substituent is preferably a substituent obtained by substituting a hydrogen atom of the hydroxyl group or amino group at the 3-position in the structural unit with a substituent represented by the general formula (II) or (III), or more preferably a substituent obtained by substituting a hydrogen atom of the hydroxyl group or amino group at the 3-position in the structural unit with a substituent represented by the general formula (II). The substituent represented by the general formula (II) is preferably a phenylcarbamoyl group, more preferably a dichlorophenylcarbamoyl group or a dimethylphenylcarbamoyl group, or still more preferably a 3,5-dichlorophenylcarbamoyl group or a 3,5-dimethylphenylcarbamoyl group.

The polysaccharide derivative of the present invention may include a structure in which a carbon atom at the 6-position in each of the structural units further has a substituent when the structural units are each a hexose. In the present invention, the substituent at the 6-position in each of the structural units is preferably a substituent obtained by substituting a hydrogen atom of the hydroxyl group or amino group at the 6-position with a substituent represented by any one of the general formulae (I) to (III); the substituent at the 6-position may be the same as the substituent at the 2-position, may be the same as the substituent at the 3-position, or may be different from these substituents.

For example, in the present invention, the substituents at the 3- and 6-positions in the structural units may be substituents obtained by substituting the hydrogen atoms of the hydroxyl groups or amino groups at the 3- and 6-positions with two kinds of substituents each represented by the general formula (II), may be substituents obtained by substituting each of the hydrogen atoms with one kind of a substituent represented by the general formula (II), or may be substituents obtained by irregularly substituting the hydrogen atoms with two or more kinds of substituents each represented by the general formula (II).

In addition, the substituent at the 3-position in each of the structural units may be a substituent obtained by substituting a hydrogen atom of the hydroxyl group or amino group at the 3-position with a substituent represented by the general formula (II), and the substituent at the 6-position in each of the structural units may be a substituent obtained by substituting a hydrogen atom of the hydroxyl group or amino group at the 6-position with a substituent represented by the general formula (I) or (III) or with a substituent represented by the general formula (III).

In addition, the substituent at the 3-position in each of the structural units may be a substituent obtained by substituting a hydrogen atom of the hydroxyl group or amino group at the 3-position with a substituent represented by the general formula (III), and the substituent at the 6-position in each of the structural units may be a substituent obtained by substituting a hydrogen atom of the hydroxy group or amino group at the 6-position with a substituent represented by the general formula (I) or (II).

The polysaccharide derivative of the present invention can be produced by the following method.

That is, the polysaccharide derivative of the present invention can be produced by a method including the steps of: modifying a hydroxyl group or amino group at the 2-position of each of the structural units of a polysaccharide with a first substituent represented by any one of the general formulae (I) to (III); and modifying a hydroxyl group or amino group at the 3-position of the structural unit with a second substituent represented by any one of the general formulae (I) to (III) and different from the first substituent. The first substituent is preferably a substituent represented by the general formula (I), and the second substituent may be a substituent represented by the general formula (I) so long as the substituent is of a structure different from that of the substituent used in the modification of the 2-position.

In the method of the present invention, the modification of a hydroxyl group or amino group with a substituent represented by any one of the general formulae can be performed by utilizing a known technique, and, furthermore, purification or fractionation as required. For example, in the case of the modification of the hydroxyl group at the 2-position with the first substituent, modification with a substituent represented by the general formula (I) can be performed by an ester exchange reaction between a carboxylic acid ester corresponding to the general formula (I) and a hydroxyl group of the polysaccharide in the presence of a low-molecular-weight salt such as disodium hydrogen phosphate or sodium carbonate as described in, for example, Non-patent Document 1. A neutral, weakly acidic, or weakly alkaline salt such as hydrogen phosphate, sulfate, chloride, and bromide, an alkaline salt such as carbonate, hydrogen carbonate, acetate, and phosphate, or the like can be used as a catalyst effective for selective introduction of the carboxylic acid ester into the 2-position in the ester exchange reaction; for example, ammonium chloride ($NH_4O_1$), sodium chloride (NaCl), sodium citrate, potassium phosphate ($K_3PO_4$), magnesium acetate, potassium carbonate ($K_2CO_3$), or sodium acetate as well as disodium hydrogen phosphate or sodium carbonate is particularly preferably used.

In the case of the modification of the amino group at the 2-position with the first substituent, modification with a substituent represented by the general formula (I) can be performed by a reaction between a primary amine and any one of the aldehydes for forming an imino bond as described in, for example, Patent Document 3. So long as the first substituent is a substituent represented by the general formula (I), one or two or more carboxylic acid esters each corresponding to the general formula (I) can be used in the introduction of the first substituent.

In the case of the modification of the hydroxyl group at the 2-position with the first substituent, modification with a substituent represented by the general formula (II) can be performed by causing an isocyanate corresponding to the general formula (II) and a hydroxyl group of the polysaccharide to react with each other under an appropriate condition with an appropriate solvent and an appropriate catalyst.

In the case of the modification of the amino group at the 2-position with the first substituent, modification with a substituent represented by the general formula (II) can be performed by causing an isocyanate corresponding to the general formula (II) and an amino group of the polysaccharide to react with each other through the application of a reaction between an amine and an isocyanate to produce urea as described in, for example, Patent Document 5.

In the case of the modification of the hydroxyl group or amino group at the 2-position with the first substituent, modification with a substituent represented by the general formula (III) can be performed by causing a halide corresponding to the general formula (III) and a hydroxyl group or amino group of the polysaccharide to react with each other under an appropriate condition in dioxane or pyridine with potassium hydroxide or potassium t-butoxide as a base.

In the case of the modification of the hydroxyl group at the 3-position with the second substituent, modification with a substituent represented by the general formula (I) can be performed by causing an acid chloride of a carboxylic acid corresponding to a substituent different from the first substituent and a hydroxyl group of the polysaccharide to react with each other in pyridine as described in, for example, Patent Document 5.

In the case of the modification of the amino group at the 3-position with the second substituent, modification with a substituent represented by the general formula (I) can be performed by causing an isocyanate corresponding to a substituent different from the first substituent and an amino group of the polysaccharide to react with each other through the application of a reaction between an amine and an isocyanate to produce urea as described in, for example, Patent Document 5.

With regard to the introduction of the second substituent, the modification of the hydroxyl group or amino group at the 3-position with a substituent represented by the general formula (II) and the modification of the hydroxyl group or amino group at the 3-position with a substituent represented by the general formula (III) can each be performed in the same manner as in the above-mentioned introduction of the first substituent.

When the structural units are each a hexose in the above-mentioned method of modifying the 3-position, the hydroxyl groups or amino groups at the 3- and 6-positions can each be modified with the second substituent by changes in reaction conditions such as an increase in the amount of a reagent (by, for example, 2 equivalents or more). In addition, when two compounds each corresponding to the second substituent are used as raw materials for introducing the second substituent, these substituents can be introduced at random in rough accordance with a raw material ratio.

For example, when an equivalent mixture of two kinds of isocyanates each corresponding to a substituent represented by the general formula (II) is used in the modification of the hydroxyl groups or amino groups at the 3-positions, or the 5— and 6-positions, a polysaccharide derivative having the following characteristic can be obtained: the hydroxyl groups or amino groups at the 3-positions, or the 3- and 6-positions are modified with substantially equal amounts of two kinds of substituents each represented by the general formula (II).

The method may further include the step of protecting a hydroxyl group or amino group at the 6-position in the structural unit with a protective group after the modification of the hydroxyl group or amino group at the 2-position. The method preferably further includes such a step from the viewpoint of the introduction of a specific substituent into only the 3-position when a hexose is used as each structural unit.

The method may further include the steps of: removing the protective group at the 6-position in the structural unit after the modification of the hydroxyl group or amino group at the 3-position; and modifying the hydroxyl group or amino group at the 6-position from which the protective group has been removed with a third substituent represented by any one of the general formulae (I) to (III) and different from the second substituent. The method preferably further includes such steps from the viewpoint of the introduction of a substituent different from that at the 3-position into the 6-position when a hexose is used as each structural unit. The modification of the hydroxyl group or amino group at the 6-position with the third substituent can be performed with a compound corresponding to a substituent different from the second substituent in the same manner as in the above-mentioned method of modifying the 3-position from the viewpoint of the introduction of different substituents into the 3- and 6-positions in ordinary cases.

The protection of the hydroxyl group at the 6-position with the protective group can be performed by causing triphenylmethyl chloride having a methoxy group as a substituent and a hydroxyl group of the polysaccharide to react with each other in the presence of pyridine as described in, for example, Non-patent Document 2. The removal of the protective group can be performed by the addition of HCl to a solution of the resultant in chloroform or THF at a temperature equal to or lower than room temperature.

When substituents each represented by any one of the general formulae (I) to (III) but different from each other are introduced as the first and second substituents, or when the substituent with which the 2-position has been already modified is removed upon modification of the 3-position, the following procedure is preferably adopted from the viewpoint of secure introduction of different substituents into the 2- and 3-positions: the hydroxyl group or amino group at the 2-position is protected with a protective group, the second substituent is introduced into the 3-position, the protective group at the 2-position is removed, and then the first substituent is introduced into the 2-position. That is, a method is preferable, which includes: a 2-position protecting step of protecting a hydroxyl group or amino group at the 2-position of each of the structural units of a polysaccharide with a protective group; a 3-position modifying step of modifying a hydroxyl group or amino group at the 3-position of the structural unit the 2-position of which has been protected with the second substituent represented by any one of the general formulae (I) to (III); a 2-position deprotecting step of removing the protective group at the 2-position in the structural unit the 3-position of which has been modified; and a 2-position modifying step of modifying the hydroxyl group or amino group at the 2-position from which the protective group has been removed with the first substituent represented by the same general formula as that of the second substituent but different from the second substituent.

A substituent having the following characteristic can be used as the protective group at the 2-position: the protective group can be removed from the 2-position to such an extent that the second substituent introduced into the 3-position is not removed upon deprotection. When the second substituent is a substituent represented by the general formula (II), such a protective group is, for example, a substituent represented by the general formula (I), or more specifically an acetyl group or the like. In addition, the deprotection of the 2-position can be performed by hydrolysis to such an extent that the second substituent is not removed from the 3-position. Such deprotection can be performed by adjusting reaction conditions such as the kind and concentration of an acid or base to be caused to exist at the time of a hydrolysis reaction, a reaction temperature, and a reaction time.

When each of the structural units is a hexose further having a hydroxyl group or amino group at its 6-position, the 3-position modifying step is preferably a step of modifying each of the hydroxyl groups or amino groups at both the 3- and 6-positions of the structural units with the second substituent represented by any one of the general formulae (I) to (III) from the viewpoint of simple modification of the hydroxyl group or amino group at the 6-position in each structural unit.

Further, when each of the structural units is a hexose, it is preferred that the 2-position deprotecting step be a step of removing both the protective group at the 2-position and the second substituent at the 6-position, and the 2-position modifying step be a step of modifying each of both the hydroxyl groups or amino groups at the 2- and 6-positions of the structural units with the first substituent from the viewpoint of simple introduction of the same substituent into each of the 2- and 6-positions when the substituents at the 2- and 3-positions are represented by the same general formula but different from each other. The deprotection of the 2-position and the demodification of the 6-position can each be performed by hydrolysis to such an extent that the second substituent at the 3-position is not removed; for example, the deprotection and the demodification can each be performed by increasing a reaction temperature and a reaction time out of the conditions for hydrolysis in a deprotecting step for only the 2-position.

Substituents represented by one of the general formulae (I) to (III) can be selected as the first and second substituents in the above-mentioned production method including protecting the 2-position. The first and second substituents may be substituents each represented by the general formula (I), may be substituents each represented by the general formula (II), or may be substituents each represented by the general formula (III). The first and second substituents are preferably substituents each represented by the general formula (II) from the viewpoint of the formation of a regular higher-order structure of the polysaccharide.

Further, when each of the structural units is a hexose, the production method including protecting the 2-position may further include: a 6-position protecting step of protecting a hydroxyl group or amino group at the 6-position of the structural unit the 2-position of which has been protected with a protective group before the 3-position modifying step; a 6-position deprotecting step of deprotecting the protective group at the 6-position in the structural unit the 3-position of which has been modified in the 3-position modifying step before the 2-position deprotecting step; and a 6-position modifying step of modifying the hydroxyl group or amino group at the 6-position from which the protective group has been removed with a third substituent represented by the same general formula as that of each of the first and second substituents but different from the first and second substituents, and the 2-position deprotecting step may be a step of removing the protective group at the 2-position in the structural unit the 6-position of which has been modified.

As described above, the following procedure is preferable from the viewpoint of the modification of the 2-, 3-, and 6-positions with different substituents: the 6-position is protected after the protection of the 2-position and before the modification of the 3-position, and the deprotection and modification of the 6-position are performed after the modification of the 3-position and before the deprotection of the 2-position. The production method is preferable from the viewpoint of the introduction of the first to third substituents represented by the same general formula and different from one another into the 2-, 3-, and 6-positions, respectively. The first to third substituents in the production method, which have only to be represented by one of the general formulae (I) to (III), are preferably substituents each represented by the general formula (II) from the viewpoint of the formation of a regular higher-order structure of the polysaccharide. In addition, the protective group at the 6-position in the production method is not particularly limited so long as the protective group is such a substituent that the 6-position can be deprotected without the removal of the protective group at the 2-position. So long as the protective group at the 6-position satisfies such a condition, the protective group at the 6-position may be identical to or different from the protective group at the 2-position, and an appropriate group selected from the above-mentioned protective groups can be used as the protective group at the 6-position.

A separating agent for optical isomers of the present invention contains the above-mentioned polysaccharide derivative of the present invention. The separating agent for optical isomers of the present invention may be constituted only of the polysaccharide derivative of the present invention, may be constituted of a carrier such as silica gel and the polysaccharide derivative of the present invention carried on the carrier, may be of an integral type to be integrally stored in a column tube, or may be of a particle shape to be packed into a column tube. The separating agent for optical isomers of the present invention can be produced in the same manner as in a known separating agent for optical isomers containing a polysaccharide derivative except that the polysaccharide derivative of the present invention is used.

To be additionally specific, the separating agent for optical isomers can be produced by causing a carrier to carry the polysaccharide derivative of the present invention, by pulverizing the polysaccharide derivative itself, or by turning the polysaccharide derivative into spherical particles by a known method (for example, Japanese Patent Application Laid-open No. Hei 7-285889). It should be noted that the term "carry" as used herein refers to a state where the polysaccharide derivative is immobilized on the carrier. A known carrying method is applicable to a method of causing the carrier to carry the polysaccharide derivative; a method such as physical adsorption between the polysaccharide derivative and the carrier, a chemical bond between the polysaccharide derivative and the carrier, a chemical bond between molecules of the polysaccharide derivative, a chemical bond between one or both of the polysaccharide derivative and the carrier, and a third component, the irradiation of the polysaccharide derivative with light, or a radical reaction is applicable (see, for example, Japanese Patent Application Laid-open No. Hei 6-93002).

Examples of the carrier include a porous organic carrier and a porous inorganic carrier, and the carrier is preferably a porous inorganic carrier. Such a porous carrier has an average pore size of preferably 1 nm to 100 µm, or more preferably 5 nm to 5 µm. A polymer substance composed of, for example, polystyrene, polyacrylamide, or polyacrylate is suitable for the porous organic carrier, and silica, alumina, zirconia, magnesia, glass, kaolin, titanium oxide, a silicate, hydroxyapatite, or the like is suitable for the porous inorganic carrier. In addition, the morphology of the above porous inorganic carrier is not limited to a particulate carrier, and may be a network inorganic carrier like an organomineral complex, or a cylindrical, monolithic inorganic carrier that can be held in a column tube, the carrier being described in, for example, Japanese Patent Application Laid-open No. 2005-17268 or Japanese Patent Application Laid-open No. 2006-150214.

Silica gel is a particularly preferable carrier, and the particles of silica gel each have a particle diameter of 1 µm to 1 mm, preferably 1 µm to 300 µm, or more preferably 1 µm to 100 µm. In addition, the carrier may be subjected to a treatment before use for improving the affinity of the carrier for the polysaccharide derivative or for improving the surface characteristics of the carrier itself. A method of treating the surface of the carrier is, for example, silane finishing with an organic silane compound or a surface treatment method by plasma polymerization. The amount of the polysaccharide derivative which the carrier carries is preferably 1 to 100 parts by mass, more preferably 5 to 60 parts by mass, or particularly desirably 10 to 40 parts by mass with respect to 100 parts by mass of the separating agent for optical isomers.

In addition, when the polysaccharide derivative itself is pulverized or turned into spherical particles, a pulverized or spherical chitosan derivative obtained by using a mortar or the like is desirably classified so that the grain sizes of the resultant particles may be uniformized.

EXAMPLES

Hereinafter, examples will be shown. However, the present invention is not limited to these examples. It should be noted that the term "$DS_n$," in each example refers to a ratio at which a hydroxyl group or amino group at an n-position in a structural unit is substituted (the number of substituents introduced per hydroxyl group or amino group at the n-position). In addition, a DS (NMR) is calculated from increases in areas of the peak of a methyl group at around 2 ppm or of a phenyl group at around 7 to 8 ppm, and the peak of an NH proton of a carbamate at around 9 to 10 ppm with reference to a glucose ring proton and a proton of a hydroxyl group at around 4 to 6 ppm. A DS (elemental analysis) is an introduction ratio calculated from an elemental analysis value. A DS (elemental analysis) at each of 3- and 6-positions is calculated on the assumption that an analysis value for nitrogen originates from an introduced substituent. In addition, a DS (elemental analysis) at a 2-position is calculated from an increase in analysis value of carbon (Co) obtained by measuring an elemental analysis value for a polysaccharide (amylose) as a raw material and an elemental analysis value for a product as a result of a substitution reaction at the 2-position (such as Intermediate Product 1-1).

light with aluminum foil, and was then subjected to a reaction at 40° C. for 168.5 hours. After the completion of the reaction, a 2-propanol (IPA)-insoluble portion was filtrated with a glass filter, whereby Intermediate Product 1-1 as a white compound was obtained. In addition, synthesis was performed in the same manner as in the foregoing under various conditions shown in Table 1 below, whereby Intermediate Products 1-2 and 1-3 were obtained. The contents of investigations on reaction conditions in Intermediate Products 1-1 to 1-3 and the results of the investigations are shown below. In addition, FIG. 1 shows the $^1$H NMR spectrum of Intermediate Product 1-1 thus obtained.

TABLE 1

Results under different reaction conditions

| Intermediate product | Amylose | Catalyst | Vinyl benzoate | Reaction temperature | Reaction time | Yield | Degree of substitution DS(NMR) |
|---|---|---|---|---|---|---|---|
| 1-1 | 1.00 g (6.17 mmol) | Na₂HPO₄ (20.0 mg) | 2.12 g (14.3 mmol) | 40° C. | 168.5 h | 1.26 g (76.8%) | 0.99 |
| 1-2 | 2.00 g (12.3 mmol) | Na₂HPO₄ (40.4 mg) | 4.20 g (28.3 mmol) | 40-50° C. | 16 + 30 h | 2.69 g (82.1%) | 1.04 |
| 1-3 | 1.01 g (6.23 mmol) | Na₂CO₃ (20.9 mg) | 2.12 g (14.3 mmol) | 40° C. | 15 h | 1.43 g (86.2%) | 1.00 |

Synthesis Example 1

Synthesis of 2-O-benzoyl amylose

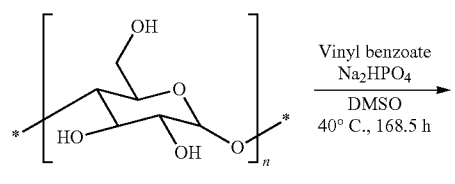

Amylose

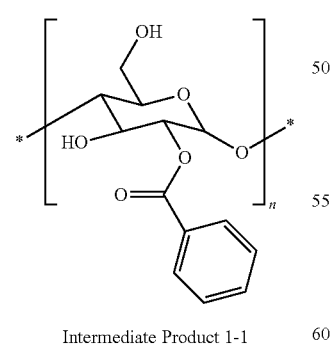

Intermediate Product 1-1

After 1.01 g (6.23 mmol, number average degree of polymerization: 300) of amylose had been dissolved in 20 mL of dehydrated dimethyl sulfoxide (DMSO), vinyl benzoate (2.3 mol/mol Anhydroglucose unit) and disodium hydrogen phosphate (2 mass % with respect to amylose) were added to the solution. The mixture was shielded from

Synthesis Example 2

Synthesis of amylose 2-benzoate-6-(3,5-dichlorophenylcarbamate)-3-(3,5-dimethylphenylcarbamate)

(1) Protection of 6-position with 4-methoxytrityl chloride

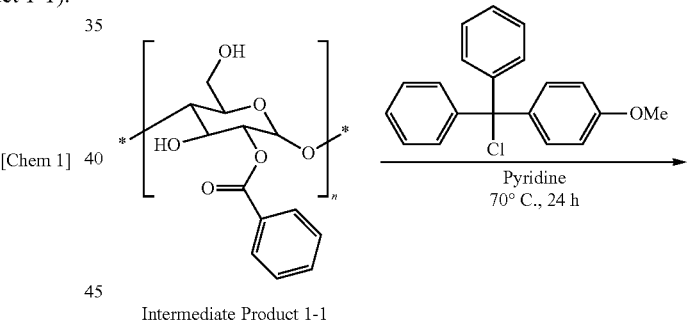

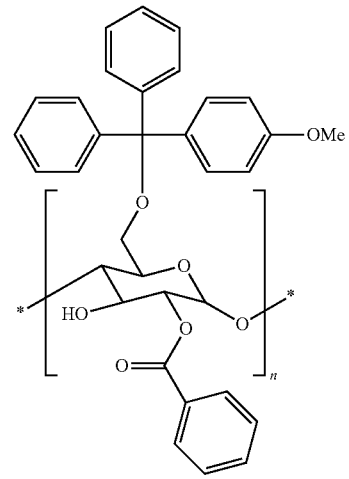

Intermediate Product 2-1

Figure 2:
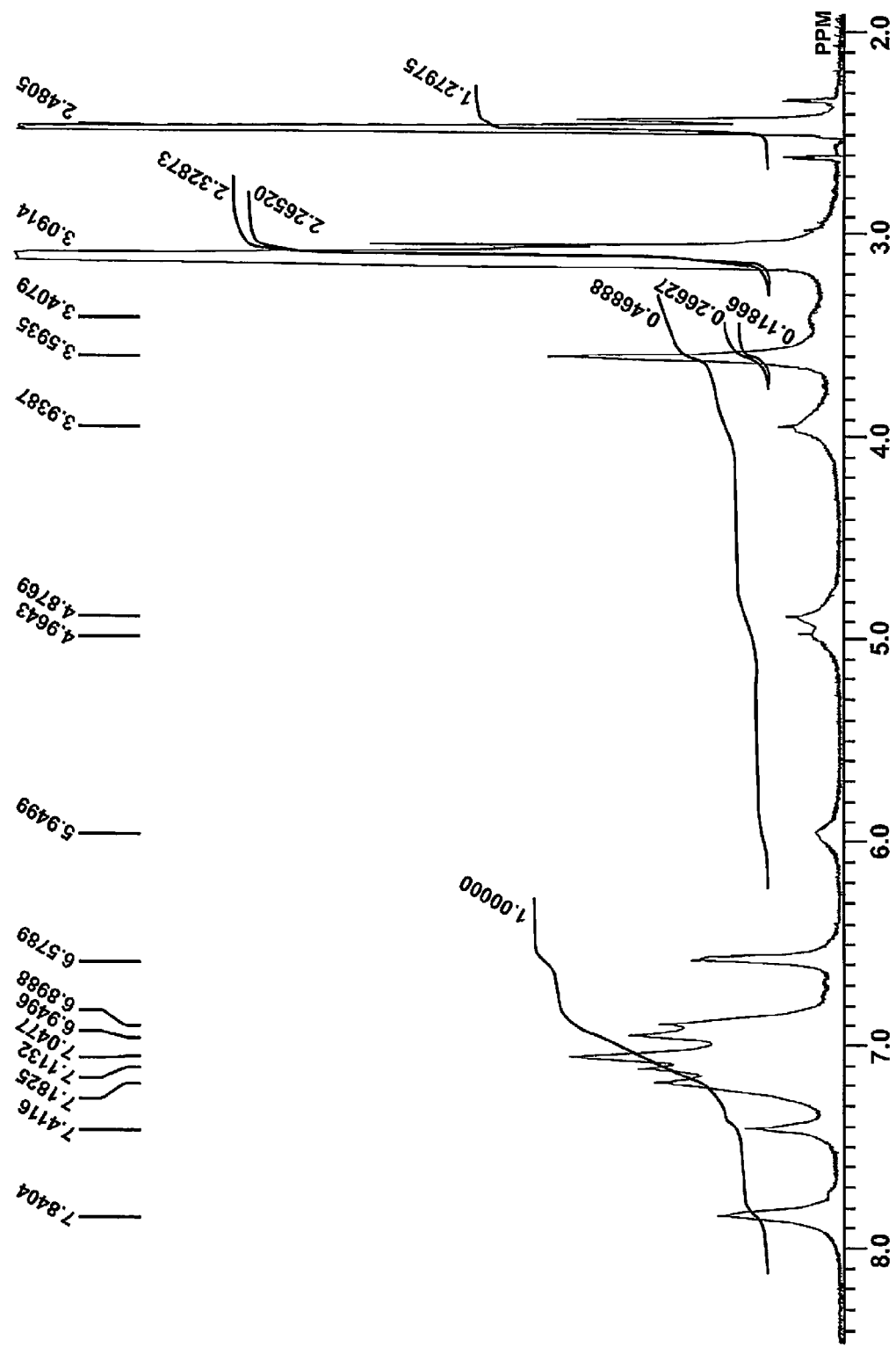
FIG. 2 is a view showing the $^1$H NMR spectrum of Intermediate Product 2-1 obtained in Synthesis Example 2 (1).

1.00 g (3.76 mmol) of Intermediate Product 1-1 was added to and dissolved in 20 mL of dehydrated pyridine. After that, 3.48 g (11.3 mmol) of 4-methoxytrityl chloride were added to the solution, and the mixture was subjected to a reaction at 70° C. for 24 hours. After the completion of the reaction, a methanol-insoluble portion was filtrated with a glass filter, whereby Intermediate Product 2-1 as a white compound was obtained. FIG. 2 shows the $^1$H NMR spectrum of Intermediate Product 2-1 thus obtained.

(2) Introduction of 3,5-dimethylphenylcarbamoyl group into 3-position

[Chem 3]

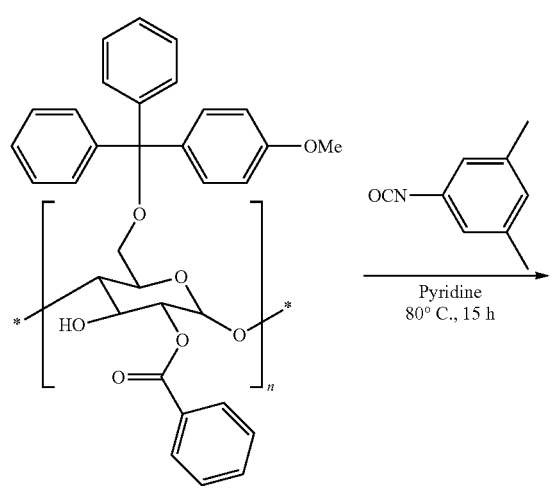

Intermediate Product 2-1

Figure 3:
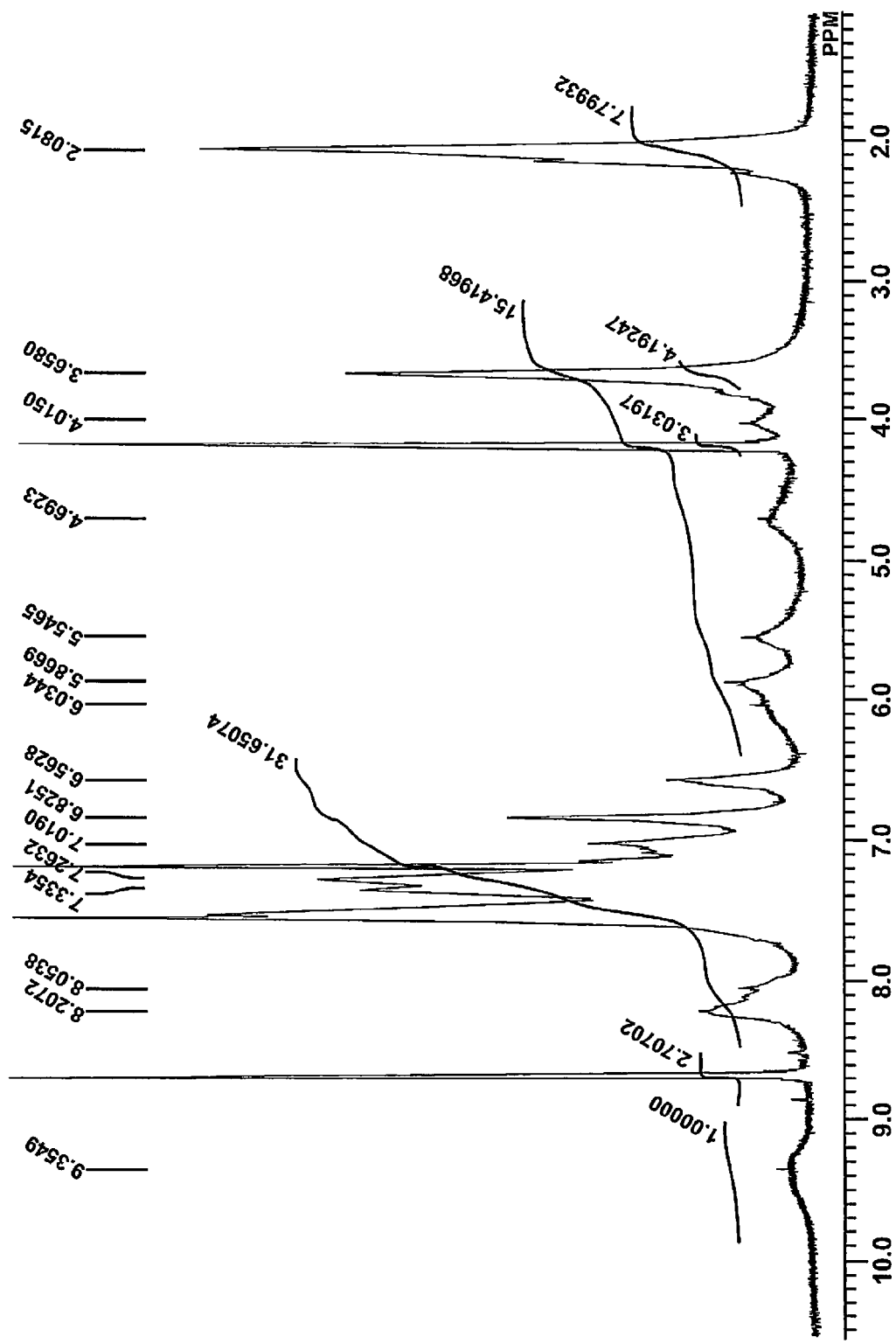
FIG. 3 is a view showing the $^1$H NMR spectrum of Intermediate Product 2-2 obtained in Synthesis Example 2 (2).

20 mL of pyridine and 0.50 g (3.36 mmol) of 3,5-dimethylphenyl isocyanate were added to 0.90 g (1.68 mmol) of Intermediate Product 2-1, and the mixture was subjected to a reaction at 80° C. for 15 hours. After the completion of the reaction, a methanol-insoluble portion was filtrated with a glass filter, whereby Intermediate Product 2-2 as a white compound was obtained. FIG. 3 shows the $^1$H NMR spectrum of Intermediate Product 2-2 thus obtained.

(3) Deprotection of 4-methoxytrityl group at 6-position

[Chem 4]

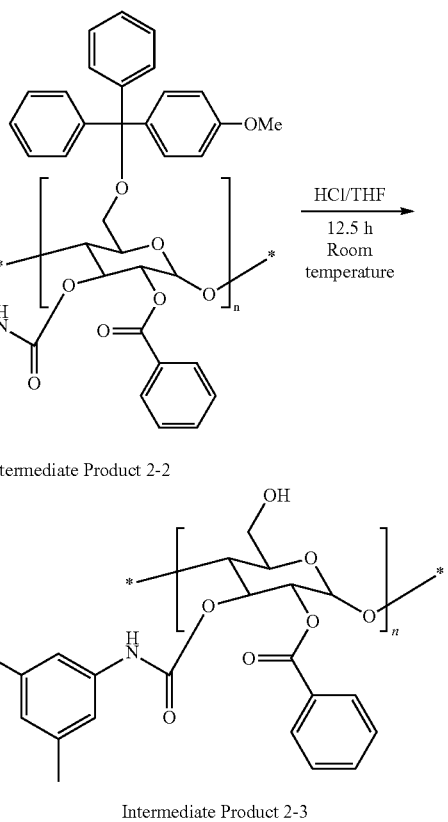

Figure 4:
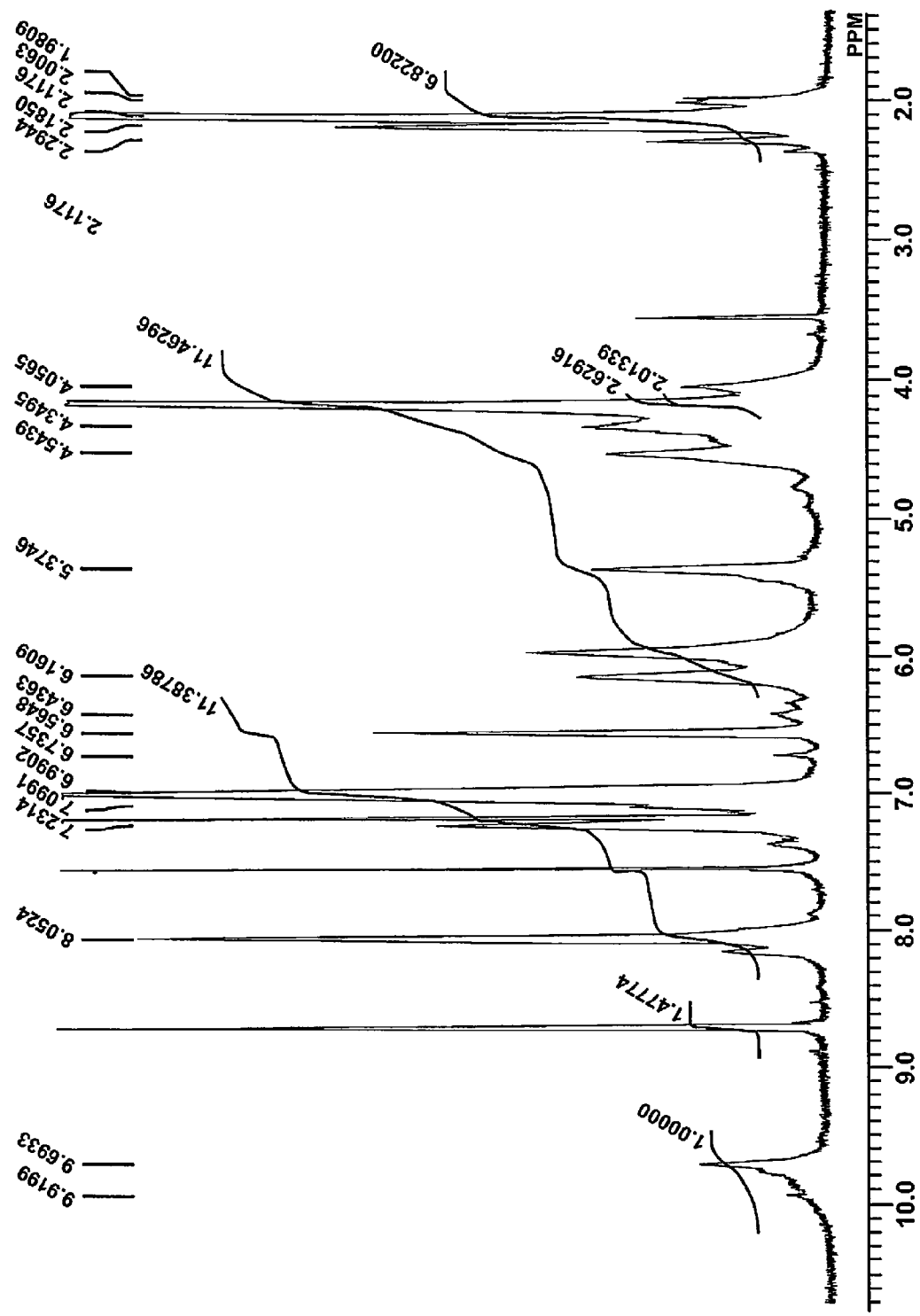
FIG. 4 is a view showing the $^1$H NMR spectrum of Intermediate Product 2-3 obtained in Synthesis Example 2 (3).

1.00 g (1.46 mmol) of Intermediate Product 2-2 was dissolved in 200 mL of THF. Next, 3.8 g (36.4 mmol) of 35% HCl were added to the solution, and the mixture was subjected to a reaction at room temperature for 12.5 hours. After the completion of the reaction, a methanol-insoluble portion was centrifuged, whereby Intermediate Product 2-3 as a white compound was obtained. The yield and physical properties of Intermediate Product 2-3 thus obtained are shown below. In addition, FIG. 4 shows the $^1$H NMR spectrum of Intermediate Product 2-3 thus obtained.

Yield: 0.58 g (96.2%)
$DS_{3-}=0.95$ (NMR)

(4) Introduction of 3,5-dichlorophenylcarbamoyl group into 6-position

[Chem 5]

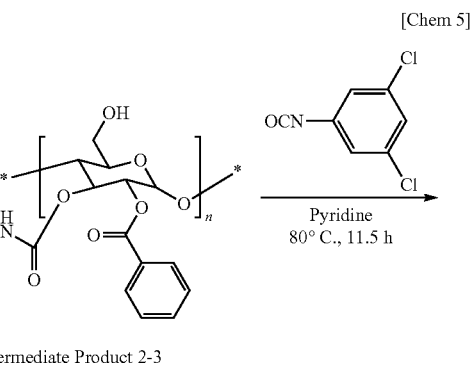

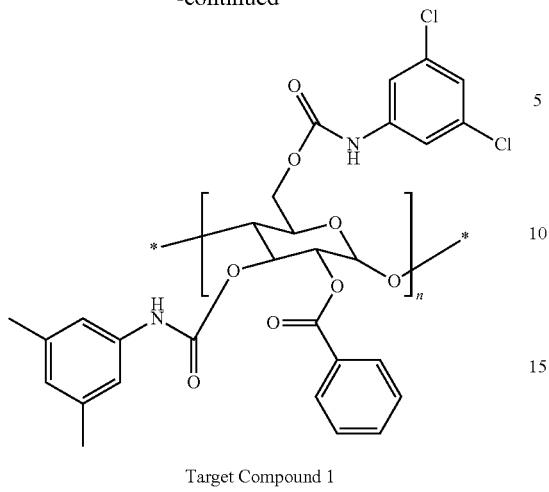

Target Compound 1

Figure 5:
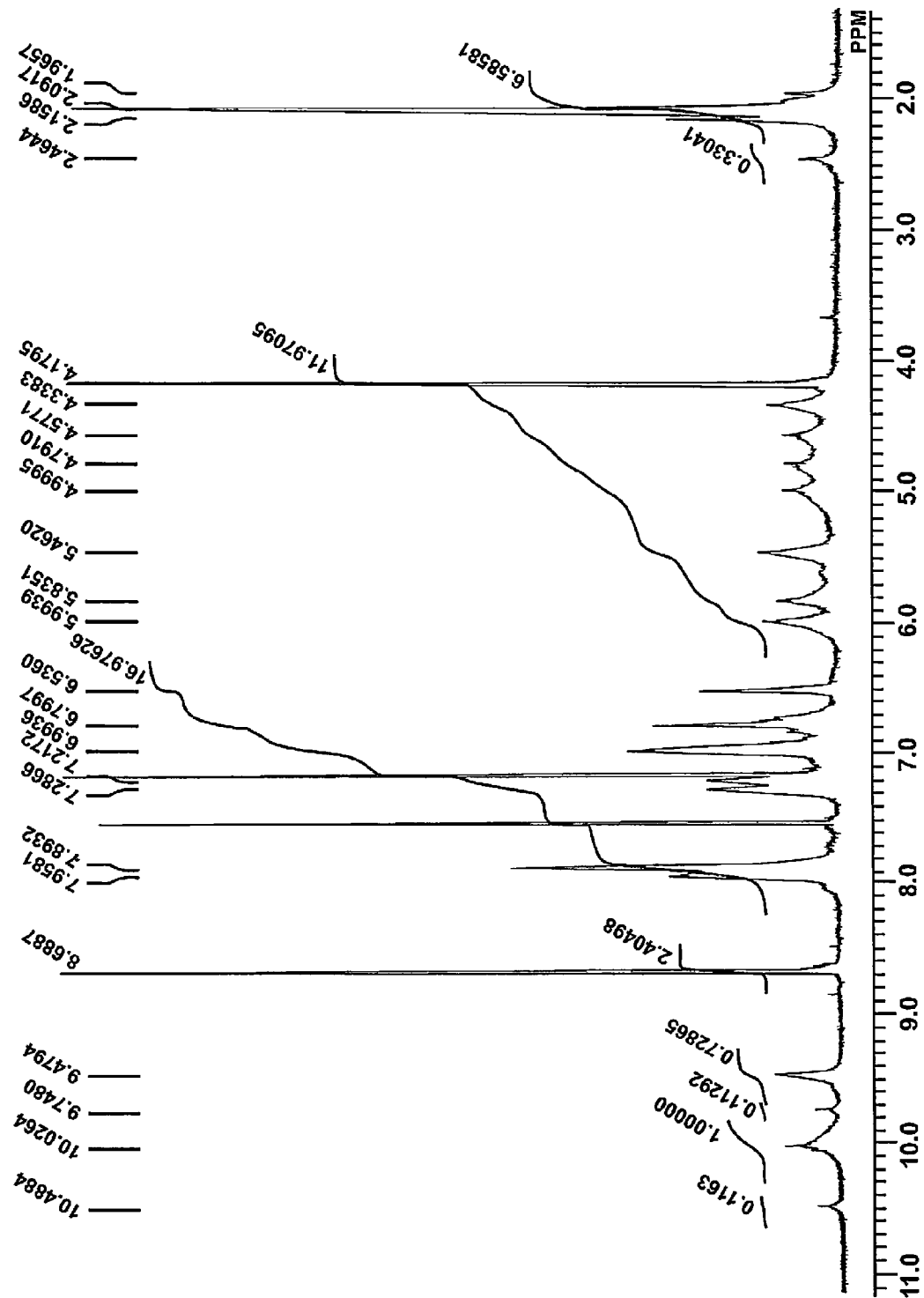
FIG. 5 is a view showing the $^1$H NMR spectrum of Target Compound 1 obtained in Synthesis Example 2 (4).

0.50 g (1.21 mmol) of Intermediate Product 2-3 was dissolved in 10 mL of pyridine. Next, 0.46 g (2.45 mmol) of 3,5-dichlorophenyl isocyanate was added to the solution, and the mixture was subjected to a reaction at 80° C. for 11.5 hours. After the peak inherent in an isocyanate of an IR spectrum had been identified by sampling, the reaction was completed, and a methanol-insoluble portion was centrifuged, whereby Target Compound 1 as a white compound was obtained. The yield and physical properties of Target Compound 1 thus obtained are shown below. In addition, FIG. 5 shows the $^1$H NMR spectrum of Target Compound 1 thus obtained.

Yield: 0.64 g (96.6%)
$DS_{6-}$=0.95 (NMR)

Synthesis Example 3

Synthesis of amylose 2-benzoate-3-(3,5-dichlorophenylcarbamate)-6-(3,5-dimethylphenylcarbamate (1) Introduction of 3,5-dichlorophenylcarbamoyl group into 3-position

[Chem 6]

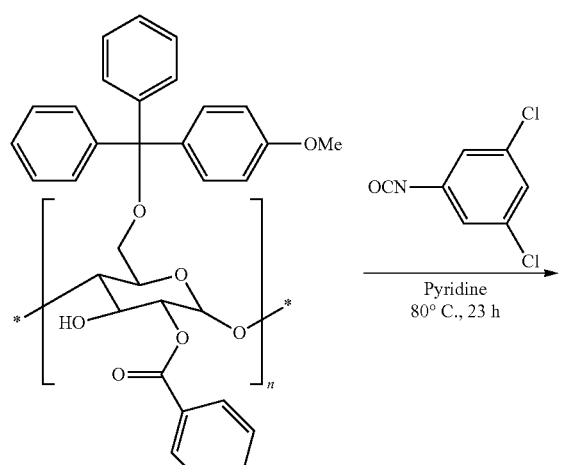

Intermediate Product 3-1

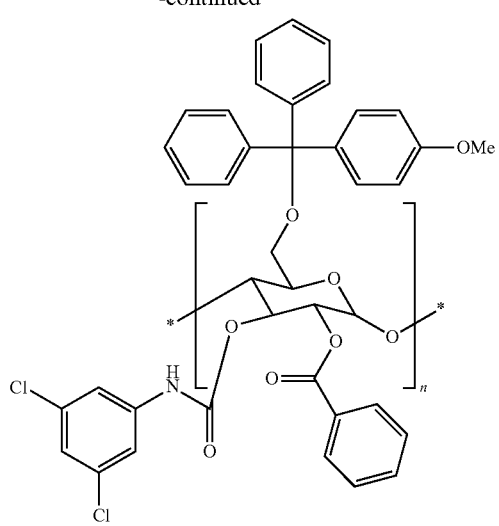

Intermediate Product 3-2

Figure 6:
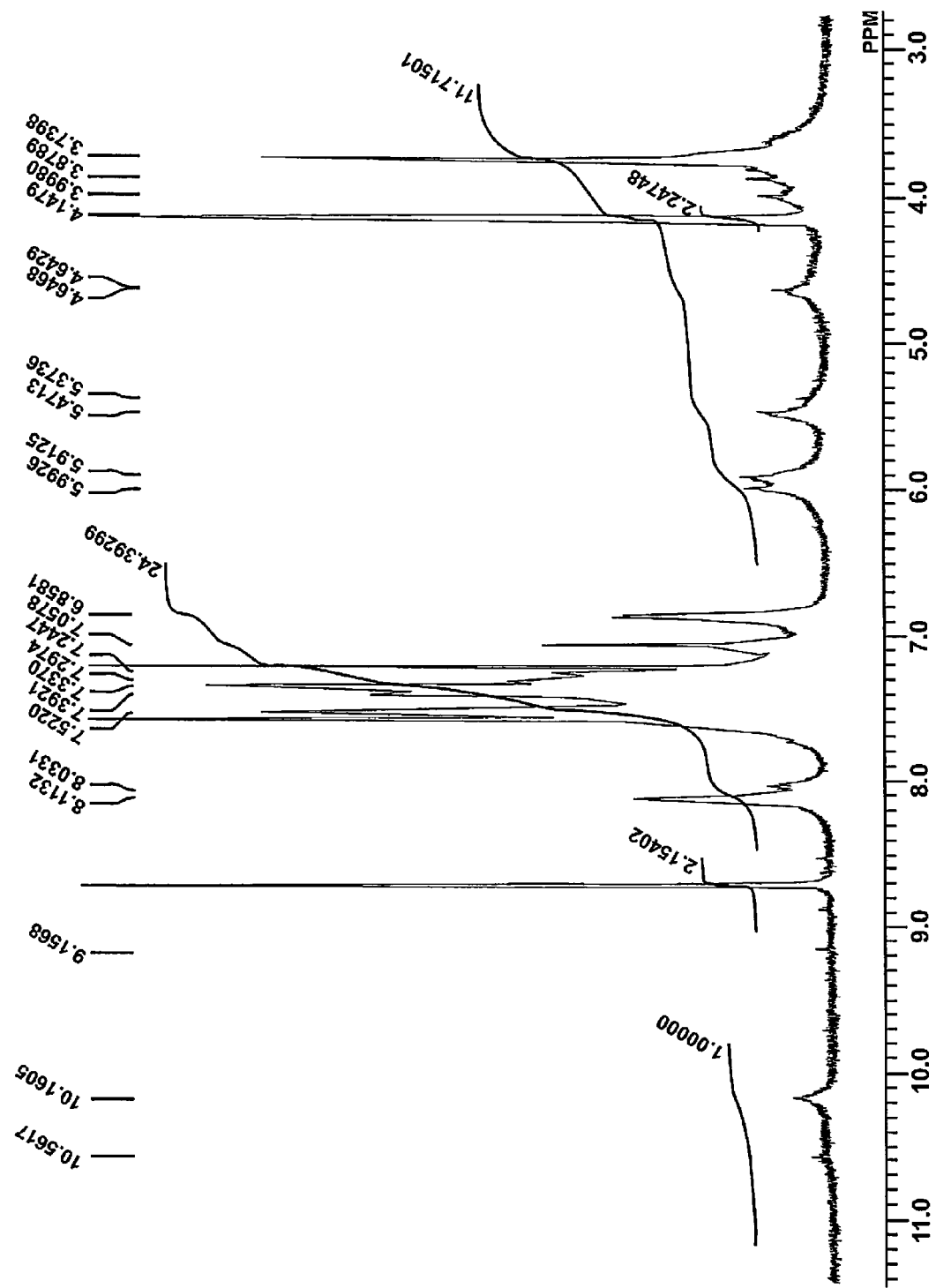
FIG. 6 is a view showing the $^1$H NMR spectrum of Intermediate Product 3-2 obtained in Synthesis Example 3 (1).

Synthesis was performed in the same manner as in the section (2) of Synthesis Example 2 under conditions in the foregoing chemical formula except that: Intermediate Product 2-1 was changed to Intermediate Product 3-1; and 3,5-dimethylphenyl isocyanate was changed to 3,5-dichlorophenyl isocyanate. Thus, Intermediate Product 3-2 as a white compound was obtained. The yield of Intermediate Product 3-2 thus obtained was 0.64 g (96.6%). In addition, FIG. 6 shows the $^1$H NMR spectrum of Intermediate Product 3-2 thus obtained.

(2) Deprotection of 4-methoxytrityl group at 6-position

[Chem 7]

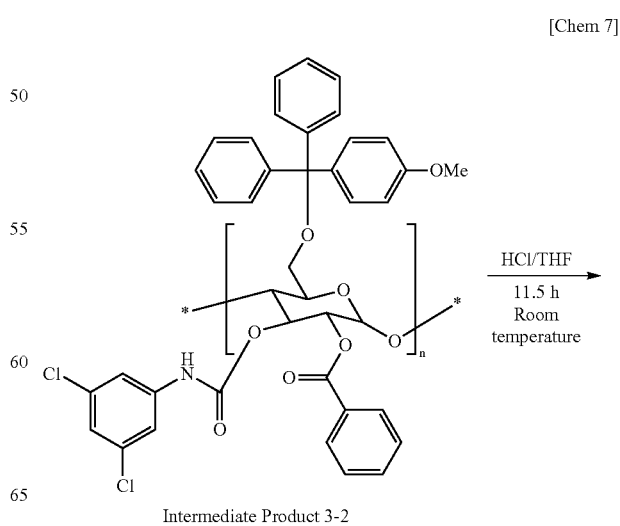

Intermediate Product 3-2

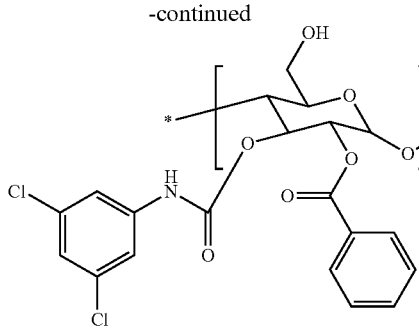

Intermediate Product 3-3

Figure 7:
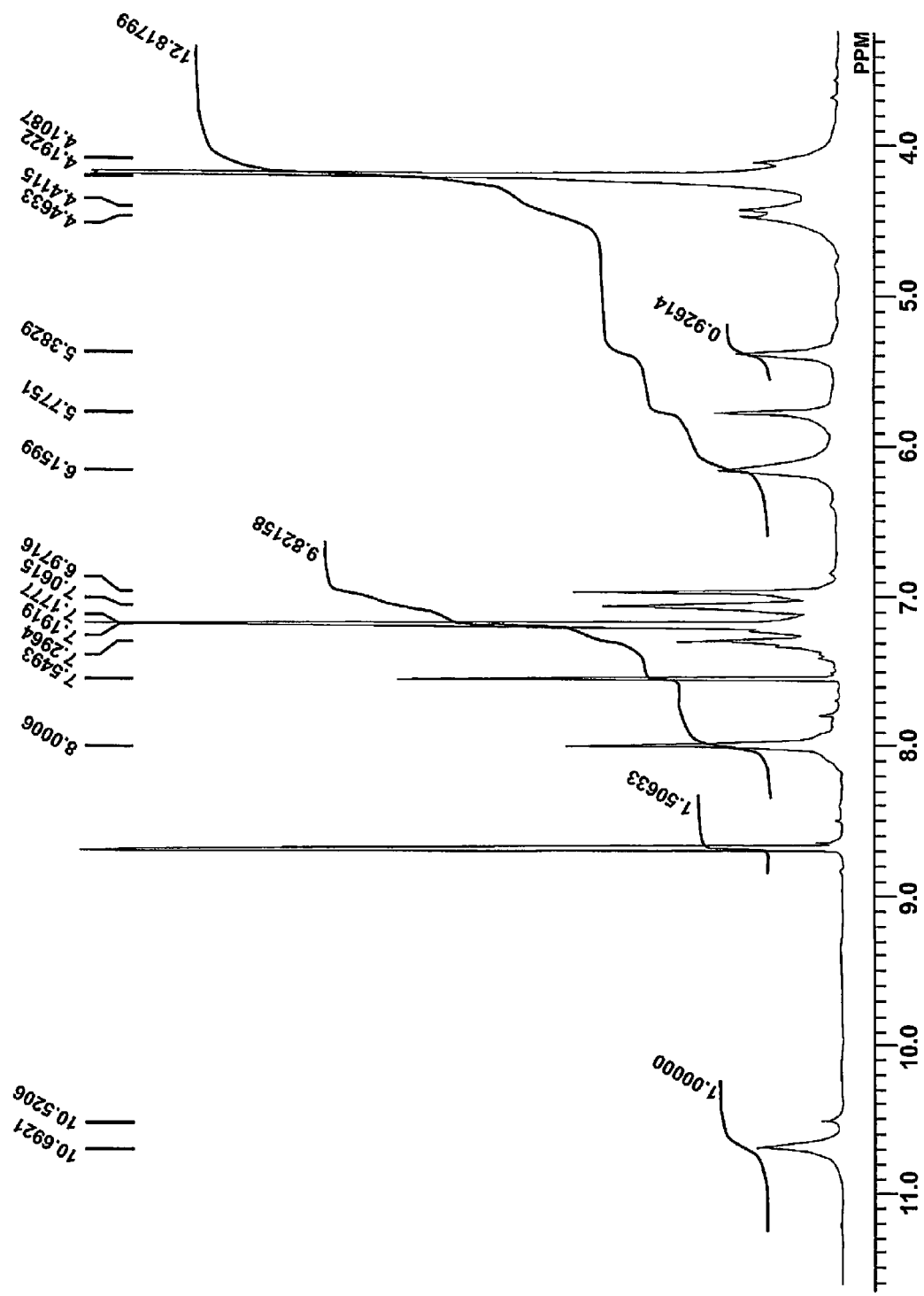
FIG. 7 is a view showing the $^1$H NMR spectrum of Intermediate Product 3-3 obtained in Synthesis Example 3 (2).

Synthesis was performed in the same manner as in the section (3) of Synthesis Example 2 under conditions in the foregoing chemical formula, whereby Intermediate Product 3-3 as a white compound was obtained. The yield and physical properties of Intermediate Product 3-3 thus obtained are shown below. In addition, FIG. 7 shows the $^1$H NMR spectrum of Intermediate Product 3-3 thus obtained.

Yield: 0.64 g (96.6%)
$DS_{3-}=0.95$ (NMR)

(3) Introduction of 3,5-dimethylphenylcarbamoyl group into 6-position

[Chem 8]

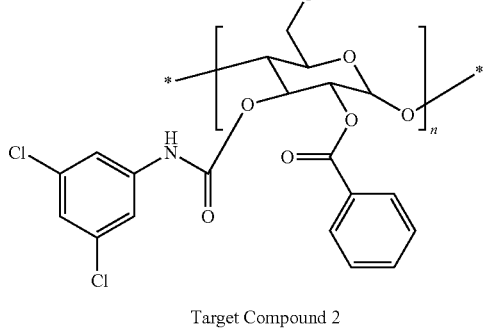

Target Compound 2

Figure 8:
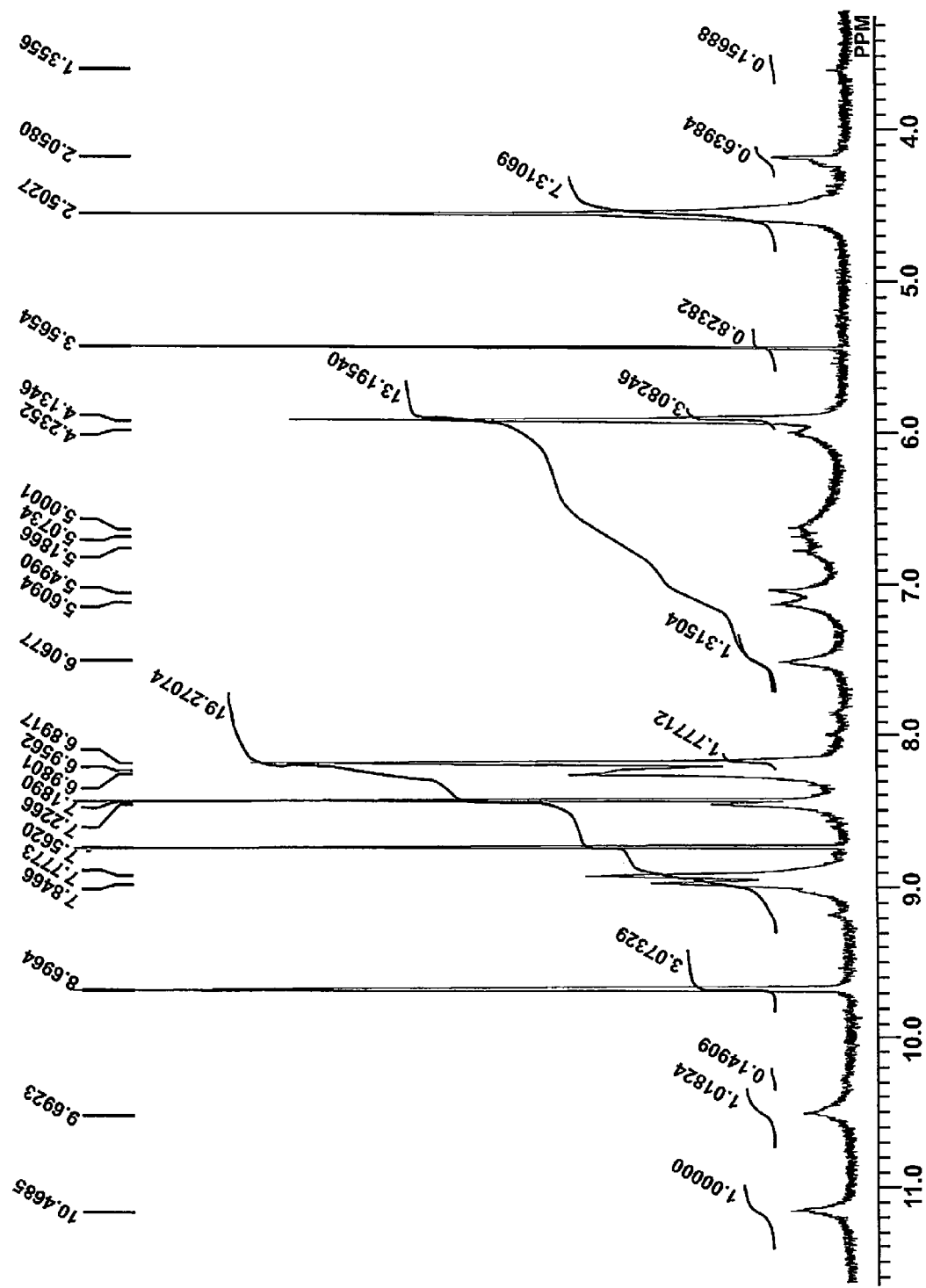
FIG. 8 is a view showing the $^1$H NMR spectrum of Target Compound 2 obtained in Synthesis Example 3 (3).

Synthesis was performed in the same manner as in the section (4) of Synthesis Example 2 under conditions in the foregoing chemical formula except that 3,5-dichlorophenyl isocyanate was changed to 3,5-dimethylphenyl isocyanate, whereby Target Compound 2 as a white compound was obtained. The yield and physical properties of Target Compound 2 thus obtained are shown below. In addition, FIG. 8 shows the $^1$H NMR spectrum of Target Compound 2 thus obtained.

Yield: 0.62 g (93.7%)
$DS_{6-}=0.93$ (NMR)

Synthesis Example 4

Synthesis of amylose 2-benzoate-3,6-random-(3,5-dimethylphenylcarbamate/3,5-dichlorophenylcarbamate)

[Chem 9]

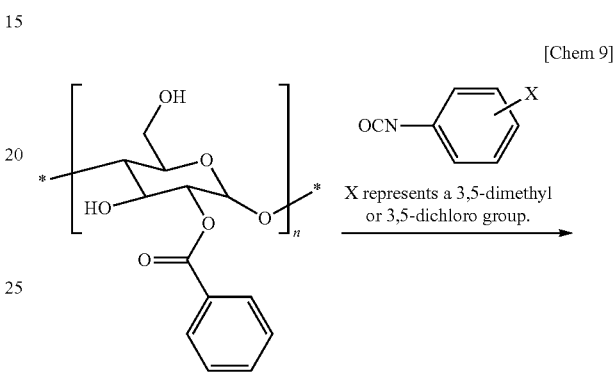

Intermediate Product 1-1

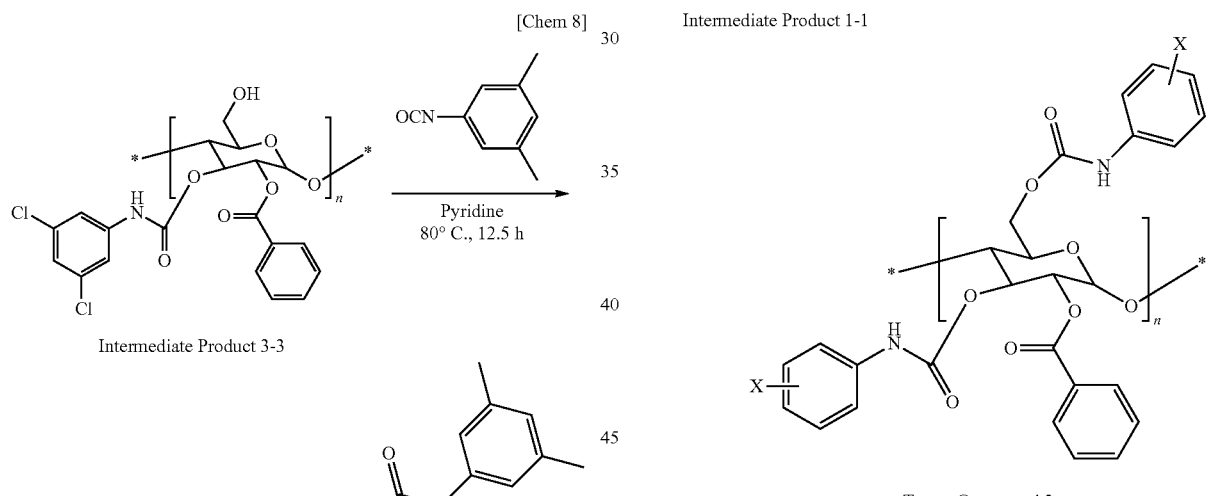

Target Compound 3

Figure 9:
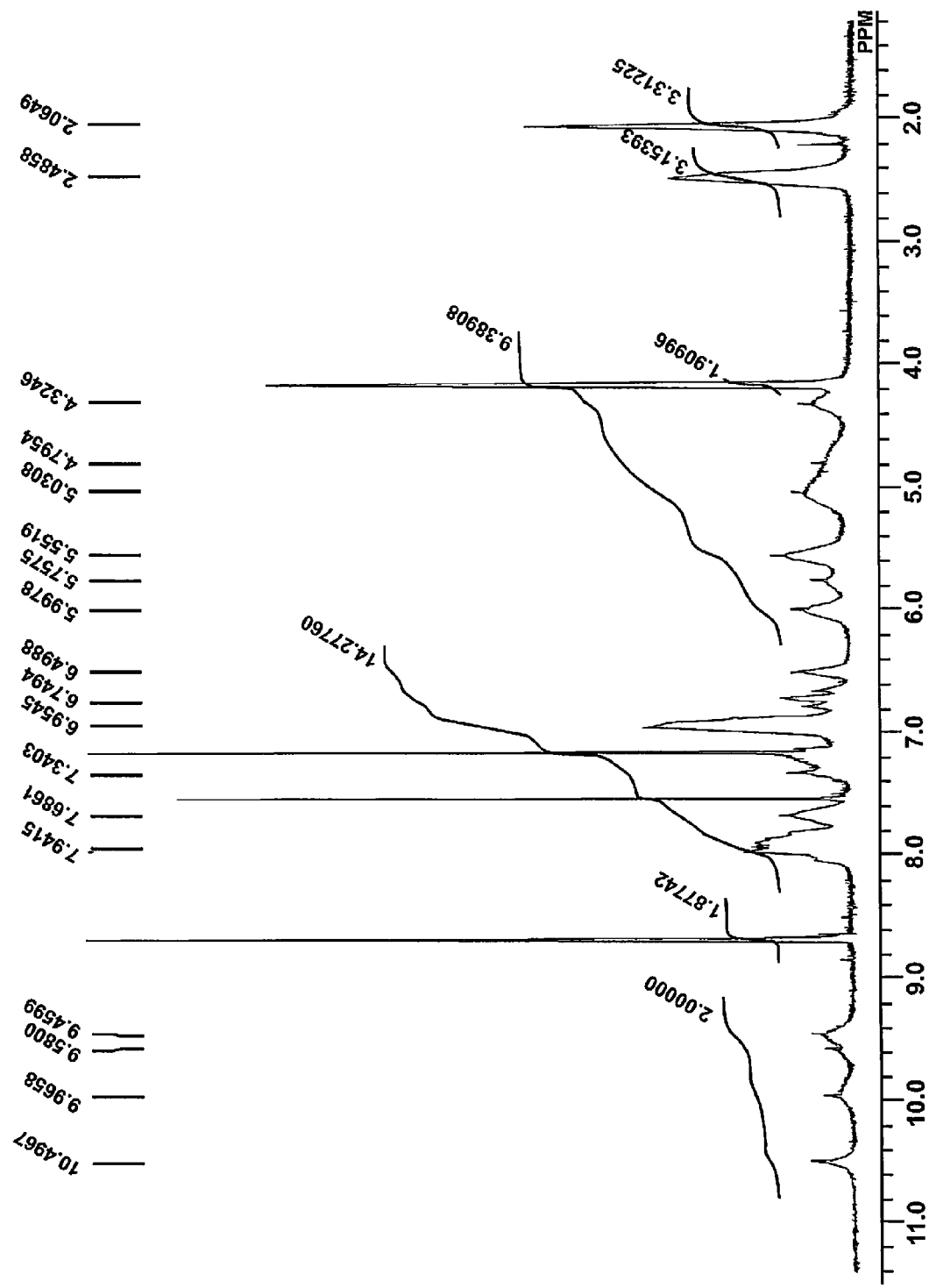
FIG. 9 is a view showing the $^1$H NMR spectrum of Target Compound 3 obtained in Synthesis Example 4.

0.50 g (1.88 mmol) of Intermediate Product 1-1 was dissolved in pyridine. About 2 equivalents of a mixture of 3,5-dimethylphenyl isocyanate and 3,5-dichlorophenyl isocyanate at a ratio of about 1:1 were gradually added to the resultant solution, and the mixture was subjected to a reaction at 80° C. for 83 hours. Thus, a derivative irregularly having two kinds of phenylcarbamoyl groups at its 3- and 6-positions was synthesized. The two kinds of phenylcarbamoyl groups were composed of a 3,5-dimethylphenylcarbamoyl group and a 3,5-dichlorophenylcarbamoyl group at a ratio of substantially 1:1, and the 3,5-dimethylphenylcarbamoyl group and the 3,5-dichlorophenylcarbamoyl group were introduced into the 3- and 6-positions of Intermediate Product 1-1, respectively. A product, i.e., Target Compound 3 as a white compound was obtained by the synthesis. The yield and physical properties of Target Compound 3 thus obtained are shown below. In addition, FIG. 9 shows the $^1$H NMR spectrum of Target Compound 3 thus obtained.

Yield: 1.09 g (96.5%)

$DS(3,5\text{-dimethyl})_{3\_}=0.51$ (NMR)

$DS(3,5\text{-dimethyl})_{6\_}=0.49$ (NMR)

Synthesis Example 5

Synthesis of amylose
2-benzoate-3,6-bis(3,5-dimethylphenylcarbamate)

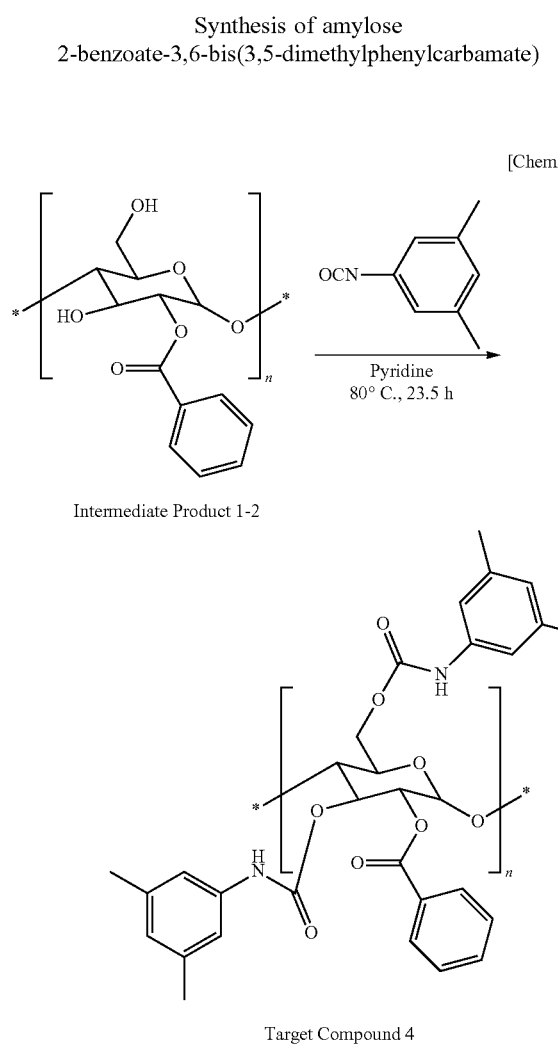

[Chem 10]

Intermediate Product 1-2

Target Compound 4

Figure 10:
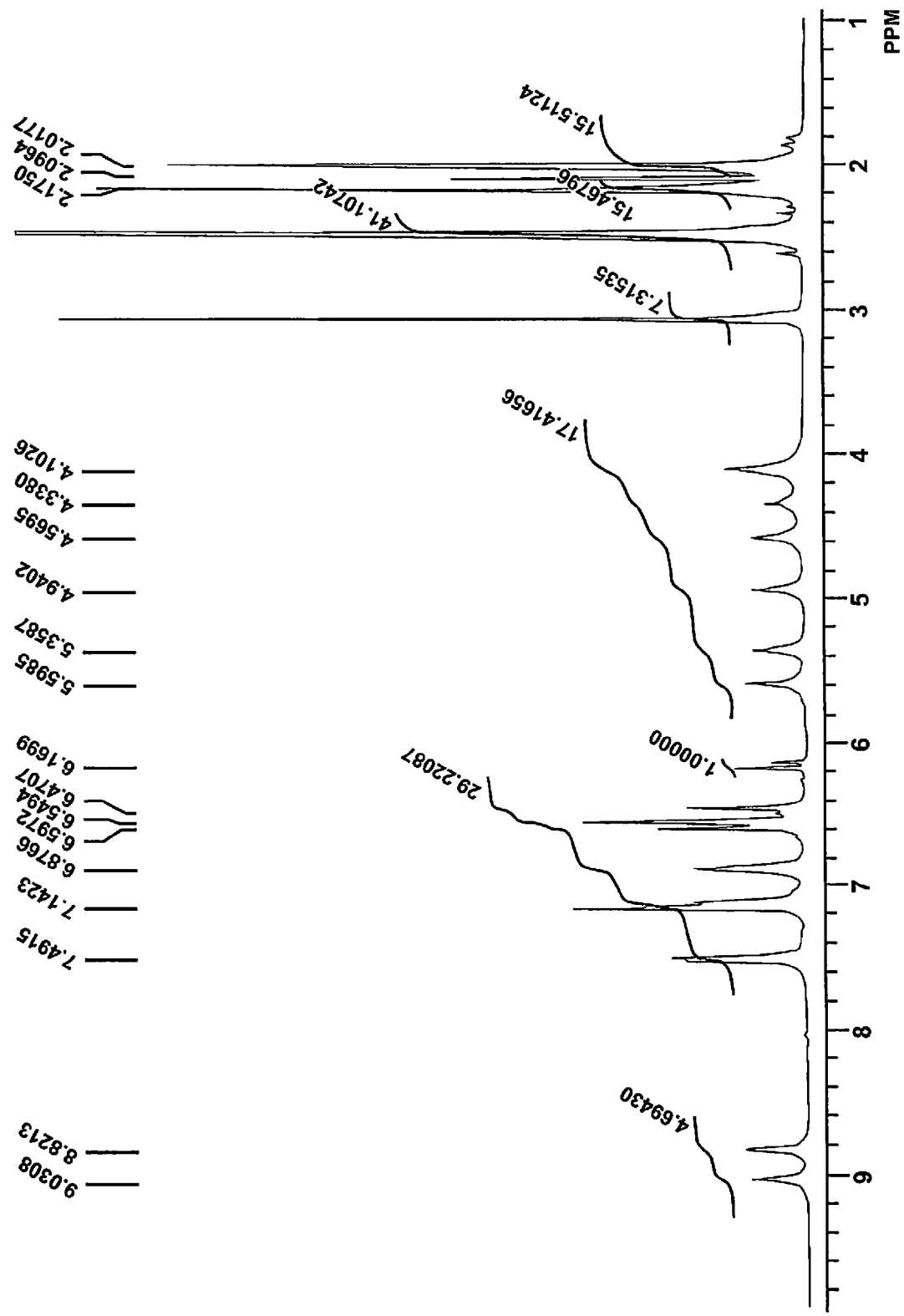
FIG. 10 is a view showing the $^1$H NMR spectrum of Target Compound 4 obtained in Synthesis Example 5.
Figure 11:
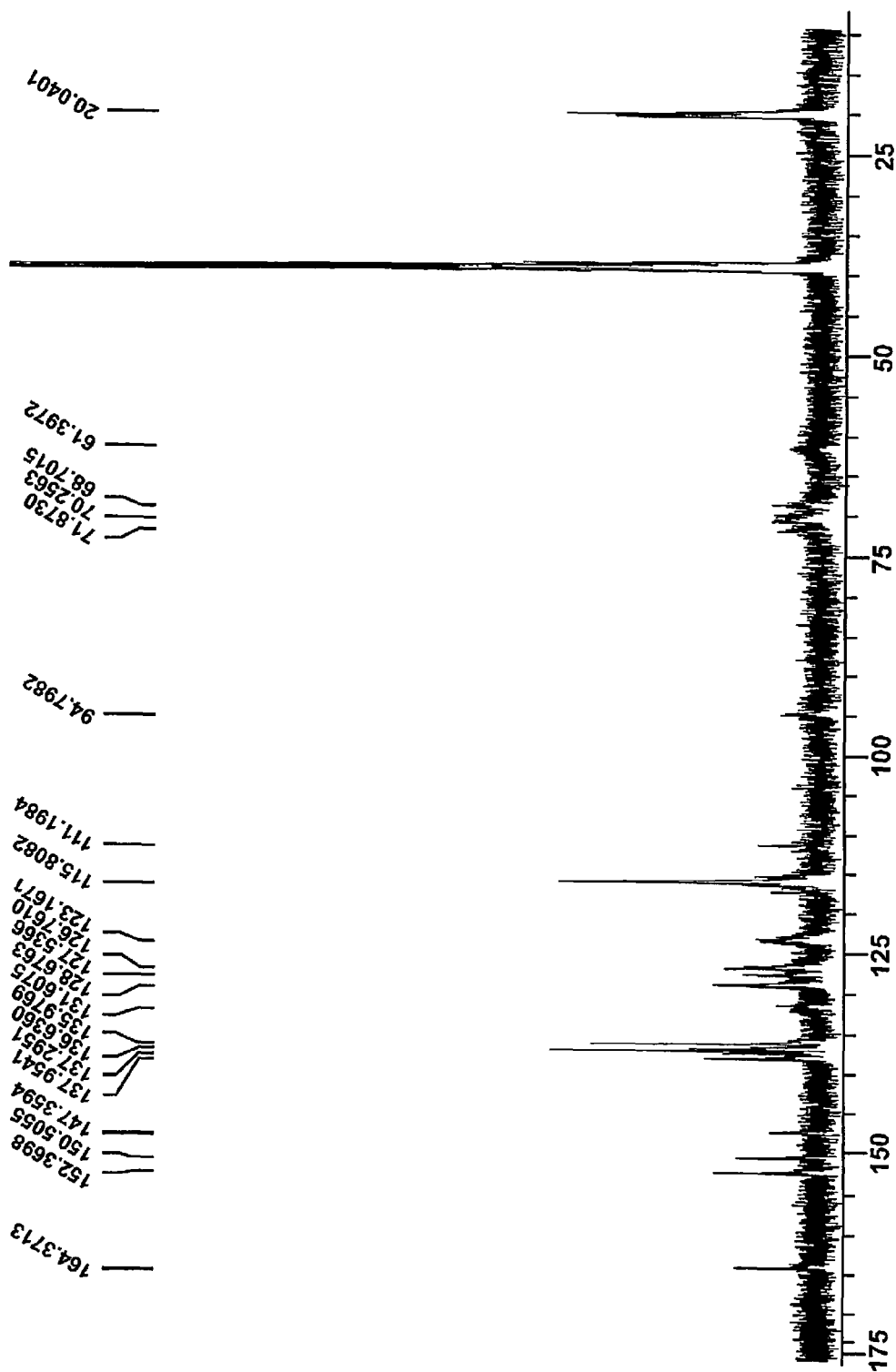
FIG. 11 is a view showing the $^{13}$C NMR spectrum of Target Compound 4 obtained in Synthesis Example 5.

1.00 g (3.76 mmol) of Intermediate Product 1-2 obtained in Synthesis Example 1 was dissolved in pyridine. 2.12 g (14.4 mmol) of 3,5-dimethylphenyl isocyanate were added to the solution, and the mixture was subjected to a reaction at 80° C. for 23.5 hours, whereby Target Compound 4 as a white compound was obtained. The yield and physical properties of Target Compound 4 thus obtained are shown below. In addition, FIG. 10 shows the $^1$H NMR spectrum of Target Compound 4 thus obtained, and FIG. 11 shows the $^{13}$C NMR spectrum of Target Compound 4.

Yield: 1.90 g (90.3%)

$DS_{2\_}=1.04/0.90$ (NMR/Elemental analysis)

$DS_{3,6\_}=1.96/2.10$ (NMR/Elemental analysis)

Elemental analysis: Analysis value C, 66.32%; H, 5.80%; and N, 5.12%

(Calculated value C, 66.42%; H, 5.75%; and N, 5.00%)

Synthesis Example 6

Synthesis of Amylose
2-benzoate-3,6-bis(3,5-dichlorophenylcarbamate)

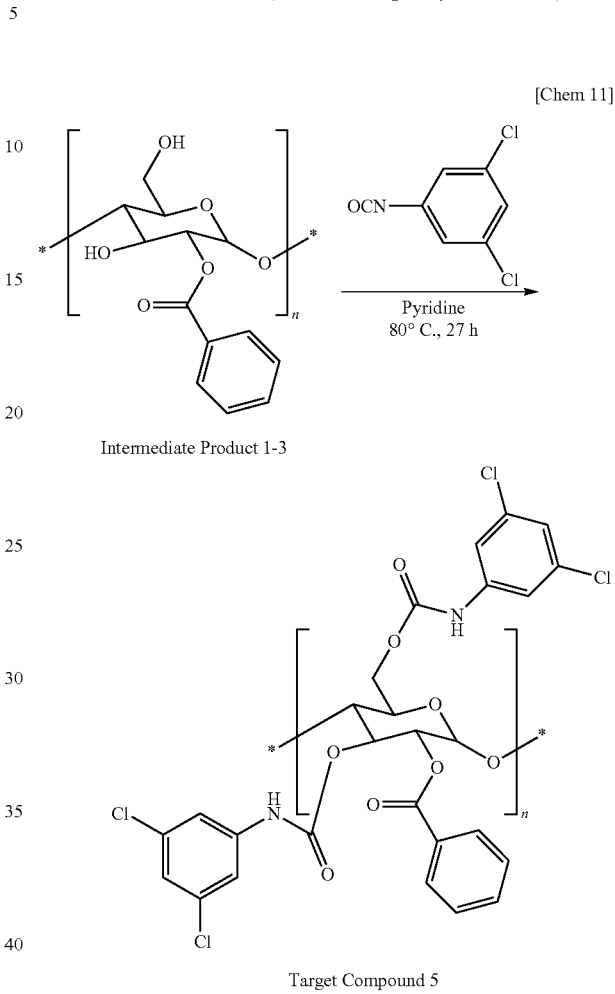

[Chem 11]

Intermediate Product 1-3

Target Compound 5

Figure 12:
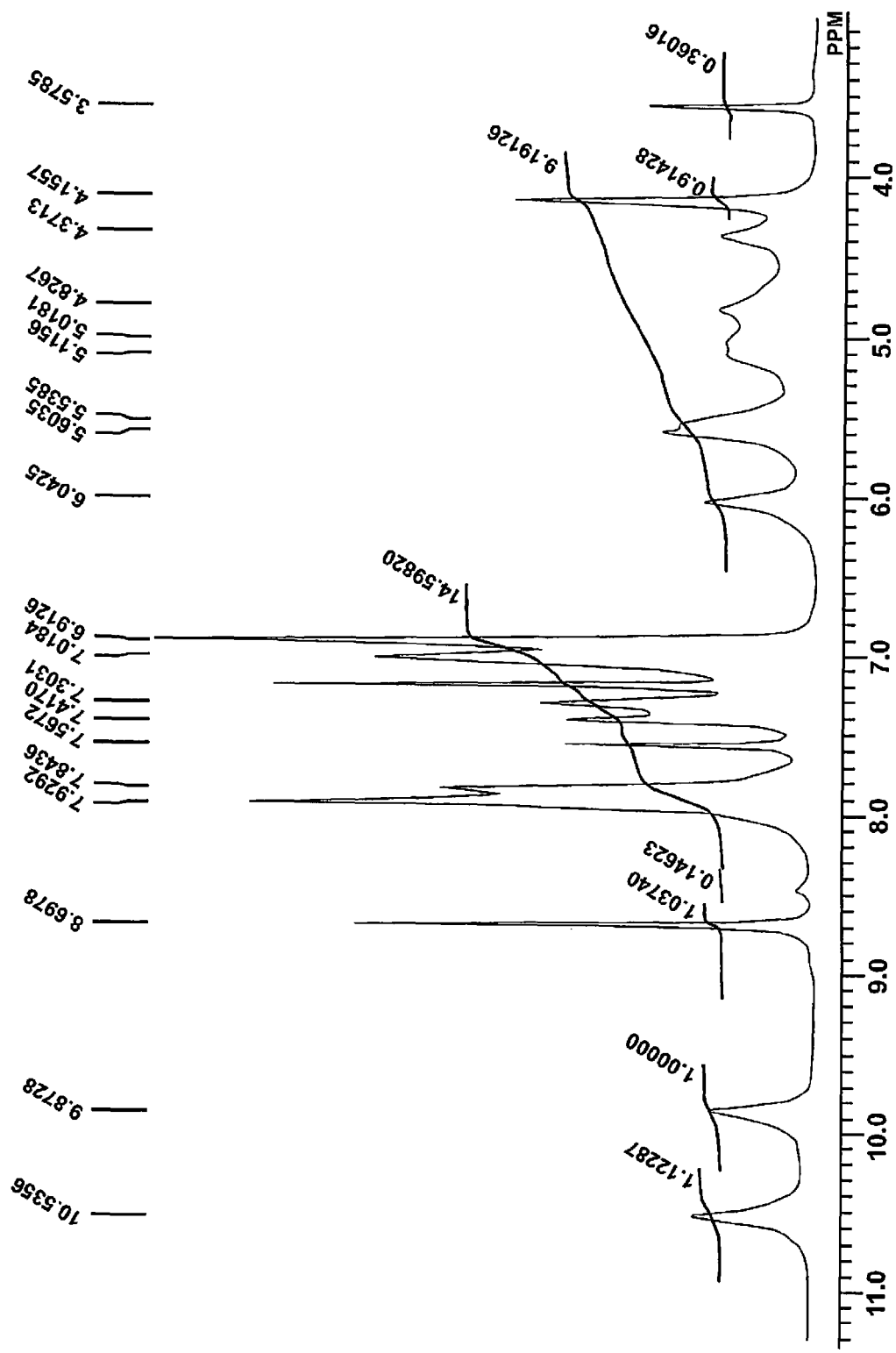
FIG. 12 is a view showing the $^1$H NMR spectrum of Target Compound 5 obtained in Synthesis Example 6.

Synthesis was performed in the same manner as in Synthesis Example 5 under conditions in the foregoing chemical formula except that: Intermediate Product 1-3 obtained in Synthesis Example 1 was used; and 3,5-dimethylphenyl isocyanate was changed to 3,5-dichlorophenyl isocyanate. Thus, Target Compound 5 as a white compound was obtained. The yield and physical properties of Target Compound 5 thus obtained are shown below. In addition, FIG. 12 shows the $^1$H NMR spectrum of Target Compound 5 thus obtained.

Yield: 2.00 g (82.8%)

$DS_{2\_}=1.00/1.23$ (NMR/Elemental analysis)

$DS_{3,6\_}=2.00/1.77$ (NMR/Elemental analysis)

Elemental analysis: Analysis value C, 50.49%; H, 3.20%; and N, 4.14%

(Calculated value C, 50.49%; H, 3.14%; and N, 4.36%)

<Production of Column for HPLC>

Silica gel the surface of which had been treated was caused to carry each of Target Compounds 1 to 5 as amylose derivatives thus obtained, and the resultant was subjected to particle diameter classification. After that, the resultant was packed into a column measuring 4.6 mm (i.d.) by 250 mm or 2.0 mm (i.d.) by 250 mm by a slurry method with an eluent composed of hexane and IPA at a ratio of 9:1, whereby a column was produced. The columns thus produced are hereinafter referred to as columns 1, 2, 3, 4, and 5.

In addition, as Comparative Examples, silica gel was similarly caused to carry each of amylose tris(3,5-dimethylphenylcarbamate) and amylose tris(3,5-dichlorophenylcarbamate), and the resultant was packed into a column, whereby a column was produced. The columns thus produced are referred to as columns 6 and 7.

<Evaluation for Optical Resolution>

Each of Target Compounds 1 to 5 synthesized here as novel amylose derivatives for use in separating agents for optical isomers was evaluated for its optical resolution with a mixed solvent of hexane and IPA at a ratio of 9:1 as an eluent and ten kinds of racemic bodies 1 to 10 shown in the following structural formula group. Table 2 shows the position and kind of a substituent in a polysaccharide derivative in each of the columns 1 to 7, and Table 3 shows the results of the evaluation for optical resolution.

In Table 3, represents a capacity ratio, and the ratio can be determined from the following equation (1) when the time period for which the eluent passes over a column is represented by $t_0$, and the time periods for which the respective enantiomers are eluted are represented by $t_1$ and $t_2$ (where $t_1 < t_2$). In addition, α represents a separation factor, and the factor can be determined from the following equation (3) by using $k_1'$ determined from the following equation (1) and $k_2'$ determined from the following equation (2).

$$k_1' = (t_1 - t_0)/t_0 \quad (1)$$

$$k_2' = (t_2 - t_0)/t_0 \quad (2)$$

$$\alpha = k_2'/k_1' \quad (3)$$

Further, the symbol "a" in Table 3 corresponds to the following conditions for the separation of optical isomers: a mixed solvent of hexane and IPA at a ratio of 9:1 is used as an eluent, a column measuring 2.0 mm (i.d.) by 250 mm is used as a column, and the flow rate of the eluent is 0.1 mL/min. The symbol "b" in Table 3 corresponds to the following conditions for the separation of optical isomers: a mixed solvent of hexane and IPA at a ratio of 9:1 is used as an eluent, a column measuring 4.6 mm (i.d.) by 250 mm is used as a column, and the flow rate of the eluent is 0.5 mL/min.

[Chem 12]

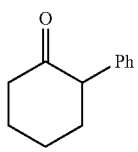

1

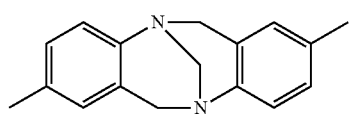

2

3

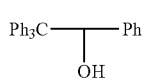

4

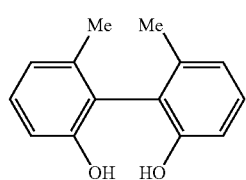

5

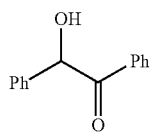

6

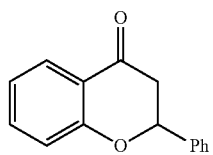

7

Co(acac)3

8

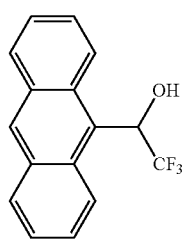

9

10

TABLE 2

Position and kind of specific substituent in polysaccharide derivative in separating agent for optical isomers

|  | Column 1 | Column 2 | Column 3 | Column 4 | Column 5 | Column 6 | Column 7 |
|---|---|---|---|---|---|---|---|
| 2-position | Benzoyloxy | Benzoyloxy | Benzoyloxy | Benzoyloxy | Benzoyloxy | 3,5-dimethyl-phenylcarbamoyl |  |
| 3-position | 3,5-Dimethyl-phenylcarbamoyl | 3,5-dichloro-phenylcarbamoyl | 3,5-dimethyl phenylcarbamoyl and | 3,5-dimethyl-phenylcarbamoyl | 3,5-dichloro-phenylcarbamoyl | 3,5-dimethyl-phenylcarbamoyl | 3,5-dichloro-phenylcarbamoyl |
| 6-position | 3,5-dichloro-phenylcarbamoyl | 3,5-dimethyl-phenylcarbamoyl | 3,5-dichloro-phenylcarbamoyl (random) | 3,5-dimethyl-phenylcarbamoyl | 3,5-dichloro-phenylcarbamoyl | 3,5-dimethyl-phenylcarbamoyl | 3,5-dichloro-phenylcarbamoyl |

TABLE 3

| Racemic body | Column 1 a) $k_1'$ | α | Column 2 a) $k_1'$ | α | Column 3 a) $k_1'$ | α | Column 4 b) $k_1'$ | α | Column 5 b) $k_1'$ | α | Column 6 b) $k_1'$ | α | Column 7 b) $k_1'$ | α |
|---|---|---|---|---|---|---|---|---|---|---|---|---|---|---|
| 1 | 1.94 (−) | 1.15 | 3.14 (+) | 1.24 | 2.52 (+) | 1.15 | 2.51 (−) | 1.03 | 4.24 (+) | ~1 | 0.61 (−) | ~1 | 1.26 (−) | ~1 |
| 2 | 1.09 (+) | 1.85 | 1.75 (+) | 2.31 | 1.39 (+) | 1.95 | 1.84 (+) | 2.08 | 1.64 (+) | 2.21 | 0.53 | 1.58 | 0.84 (+) | 1.34 |
| 3 | 0.70 (−) | 1.30 | 1.31 (−) | ~1 | 1.07 (−) | 1.13 | 1.82 (+) | 1.08 | 1.13 (−) | 1.44 | 0.42 (+) | 3.04 | 0.50 (+) | 1.32 |
| 4 | 1.30 (+) | 1.07 | 2.01 (+) | 1.22 | 1.71 (+) | 1.18 | 2.76 (+) | 1.05 | 1.53 (+) | 1.34 | 2.65 (+) | 1.98 | 0.88 (+) | 2.25 |
| 5 | 2.02 (−) | 1.11 | 2.95 (−) | 1.12 | 2.19 (−) | 1.10 | 4.28 (−) | 1.09 | 3.30 (+) | ~1 | 2.46 (−) | 2.11 | 1.10 (+) | ~1 |
| 6 | 3.28 (−) | 1.73 | 8.45 (−) | 1.97 | 5.04 (−) | 1.87 | 5.70 (−) | 1.63 | 7.48 (−) | 1.89 | 3.14 (−) | 1.21 | 6.08 (+) | ~1 |
| 7 | 2.33 (−) | 1.17 | 3.60 (+) | 1.13 | 3.16 (−) | 1.03 | 4.72 (−) | 1.06 | 3.53 (−) | 1.20 | 0.93 (+) | 1.12 | 1.62 (+) | 1.10 |
| 8 | 0.99 (−) | 1.75 | 1.45 (−) | 2.46 | 0.93 (−) | 2.21 | 1.15 (−) | 2.10 | 1.41 (−) | 1.80 | 0.25 (−) | ~1 | 0.63 (+) | ~1 |
| 9 | 0.65 (−) | 1.18 | 0.84 (+) | 1.23 | 0.69 (+) | 1.12 | 1.85 | 1.00 | 0.62 | 1.00 | 1.30 (+) | 1.15 | 0.37 | 1.00 |
| 10 | 1.31 (+) | 3.21 | 6.72 (+) | 3.71 | 1.77 (+) | 5.23 | 2.53 (+) | 3.56 | 1.07 (+) | 3.79 | 3.25 (+) | 2.01 | 0.59 (−) | 1.11 |
| α (average) | 1.55 | | 1.74 | | 1.80 | | 1.57 | | 1.67 | | 1.62 | | 1.21 | |

The column 1 shows a higher separation factor for each of the racemic bodies 1, 2, and 6 to 10 than the column 6 does, and hence the column 1 has a better optical resolution for each of these racemic bodies than the column 6 does. In addition, the column 4 shows a higher separation factor for each of the racemic bodies 1, 2, 6, 8, and 10 than the column 6 does, and hence the column 4 has a better optical resolution for each of these racemic bodies than the column 6 does. In particular, the columns 1 and 4 each show a high separation factor for each of the racemic bodies 1 and 8 for which the column 6 does not show sufficient separation factors.

The column 2 shows a higher separation factor for each of the racemic bodies 1, 2, and 5 to 10 than the column 7 does, and hence the column 2 has a better optical resolution for each of these racemic bodies than the column 7 does. In addition, the column 5 shows a higher separation factor for each of the racemic bodies 2, 3, 6 to 8, and 10 than the column 7 does, and hence the column 5 has a better optical resolution for each of these racemic bodies than the column 7 does. In particular, the columns 2 and 5 each show a high separation factor for each of the racemic bodies 6 and 8 for which the column 7 does not show sufficient separation factors.

The column 3 shows a higher separation factor for each of the racemic bodies 1, 2, 6, 8, and 10 than each of the columns 6 and 7 does, and hence the column 3 has a better optical resolution for each of these racemic bodies than each of the columns 6 and 7 does. In particular, the separation factor of the column 3 for the racemic body 10 is much larger than those of the columns 6 and 7, and hence the column 3 shows a higher optical resolution for the racemic body 10 than each of the columns 6 and 7 does.

In addition, the average of separation factors in each of the columns 1 to 5 is comparable to or higher than the average of separation factors in each of the columns 6 and 7. Accordingly, it can be said that each of the columns 1 to 5 is comparable or superior in universality in optical resolution to the columns 6 and 7.

Synthesis Example 7

Synthesis of Intermediate Product 4-3 (amylose 3,6-bis(3,5-dimethylphenylcarbamate))

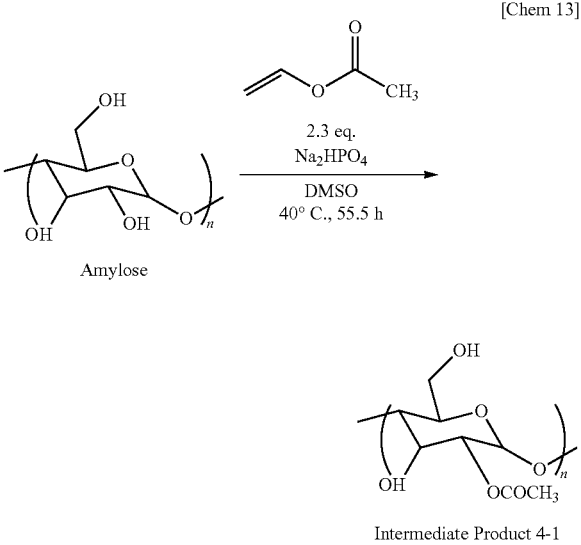

After 3.00 g (18.5 mmol) of amylose had been dissolved in 60 mL of dehydrated dimethyl sulfoxide (DMSO), 3.93 mL (42.6 mmol, 2.3 mol equivalents with respect to an anhydroglucose unit) of vinyl acetate and 60 mg (2 mass % with respect to amylose) of disodium hydrogen phosphate were added to the solution. A container storing the mixture was shielded from light with aluminum foil, and the mixture was then subjected to a reaction at 40° C. for 55.5 hours. After the completion of the reaction, a 2-propanol-insoluble portion was filtrated with a glass filter, whereby Intermediate Product 4-1 as a white compound was obtained (in substantially 100% yield).

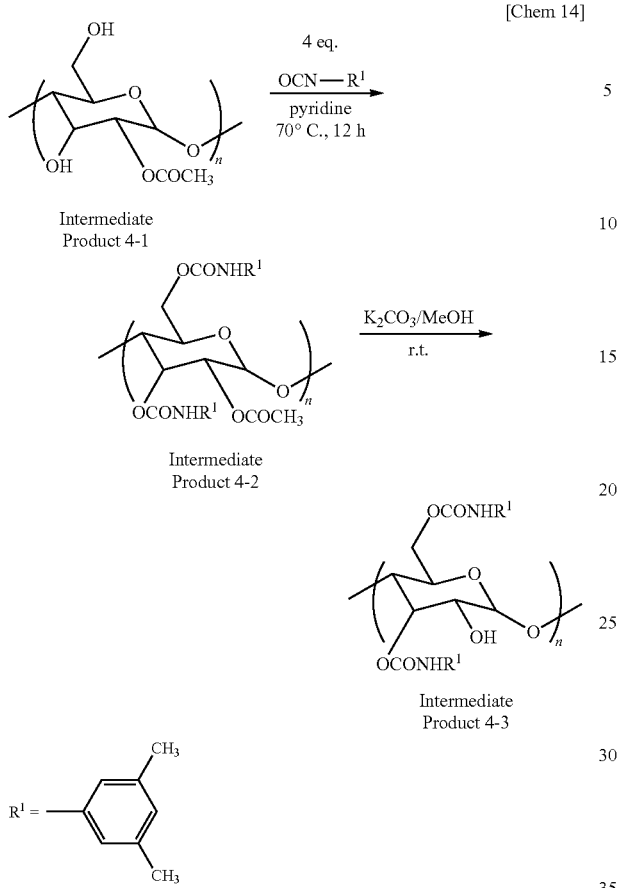

Intermediate Product 4-1

Intermediate Product 4-2

Intermediate Product 4-3

TABLE 4

| Kind of intermediate product obtained | Reaction conditions | | | |
|---|---|---|---|---|
| | Concentration of potassium carbonate in methanol solution (mass %) | Reaction time (hour(s)) | Yield (%) | Hydrolysis ratio (%) |
| 4-3-1 | 1.0 | 1 | 96.8 | 75 |
| 4-3-2 | 1.0 | 2 | 103.0 | 86 |
| 4-3-3 | 1.0 | 3 | 54.6 | 88 |
| 4-3-4 | 1.0 | 5 | 99.7 | 98 |
| 4-3-5 | 1.0 | 6 | 81.2 | 95 |
| 4-3-6 | 1.0 | 8 | 83.0 | >100 |
| 4-3-7 | 1.0 | 12 | 77.1 | >100 |
| 4-3-8 | 1.5 | 5 | 83.7 | 100 |

Synthesis Example 8

Synthesis of Target Compound 5 (amylose 2-(3,5-dichlorophenylcarbamate)-3,6-bis(3,5-dimethylphenylcarbamate)

Figure 13:
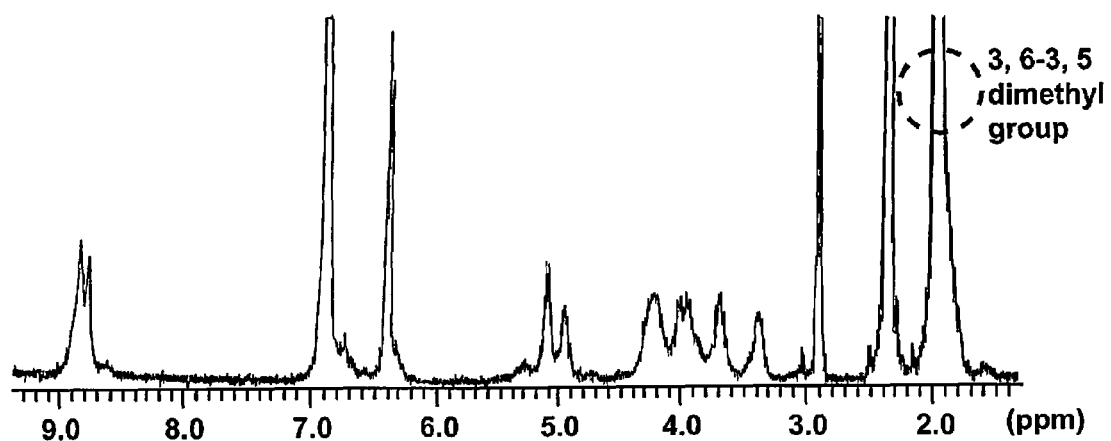
FIG. 13 is a view showing the $^1$H NMR spectrum of Intermediate Product 4-3 obtained in Synthesis Example 7.
Figure 14:
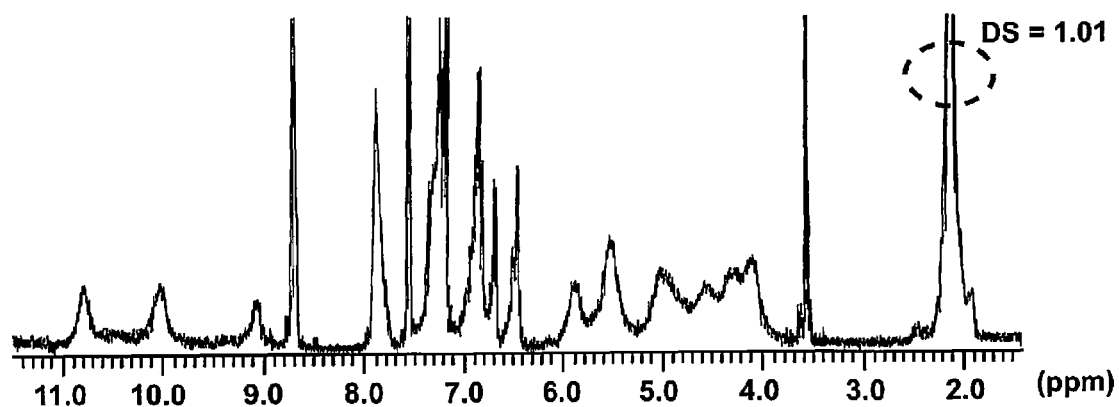
FIG. 14 is a view showing the $^1$H NMR spectrum of Target Compound 6 obtained in Synthesis Example 9.

1.50 g (7.35 mmol) of Intermediate Product 4-1 were dissolved in 30 mL of pyridine, and the solution and 2.83 mL (29.4 mmol) of 3,5-dimethylphenyl isocyanate (4 equivalents with respect to Intermediate Product 4-1) were caused to react with each other at 70° C. for 12 hours. Thus, Intermediate Product 4-2 obtained by introducing 3,5-dimethylphenylcarbamoyl groups into hydroxyl groups at the 3- and 6-positions of Intermediate Product 4-1 was synthesized (95.9% yield). Meanwhile, 24 mL of an aqueous solution of potassium carbonate prepared to have a concentration of 10 mass % were charged into 240 mL of methanol, and the mixture was stirred at 60° C., whereby a solution of potassium carbonate in methanol was prepared. Hydrolysis was performed by: dissolving 0.3 g of Intermediate Product 4-2 in 4.8 mL of THF; and dropping the solution in the solution of potassium carbonate in methanol. The mixture was subjected to a reaction in a heterogeneous system at room temperature for 6 hours so that an ester group at a 2-position of Intermediate Product 4-2 might be selectively hydrolyzed. Thus, Intermediate Product 4-3 was obtained. FIG. 13 shows the $^1$H NMR spectrum of Intermediate Product 4-3 thus obtained.

In addition, Intermediate Product 4-2 was hydrolyzed while the concentration of potassium carbonate in the solution of potassium carbonate in methanol and a reaction time for the hydrolysis were changed as shown in Table 4 below. Table 4 shows a yield and a hydrolysis ratio in each case. Here, the hydrolysis ratio was calculated from a ratio of the peak of an acetyl group (about 1.8 ppm) in a $^1$H NMR spectrum to the peak of a glucose ring (about 4 to 6 ppm) in the spectrum.

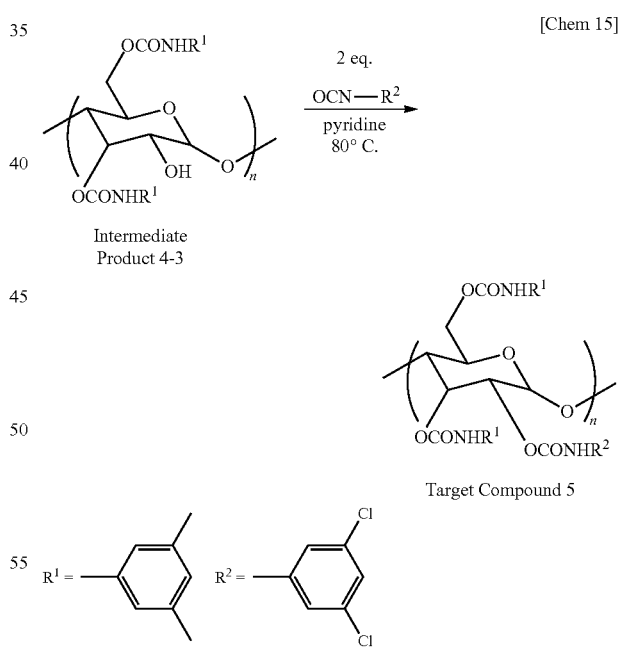

Intermediate Product 4-3

Target Compound 5

0.25 g of Intermediate Product 4-3 was dissolved in 5 mL of pyridine, and 0.15 mL (1.10 mmol) of 3,5-dichlorophenyl isocyanate was added to the solution at room temperature. Next, a container storing the mixture was immersed in an oil bath at 80° C., and then a reaction was initiated. After the completion of the reaction, a methanol-insoluble portion was recovered, whereby Target Compound 5 was obtained.

Synthesis Example 9

Synthesis of Target Compound 6 (amylose 2-(3,5-dimethylphenylcarbamate)-3,6-bis(3,5-dichlorophenylcarbamate)

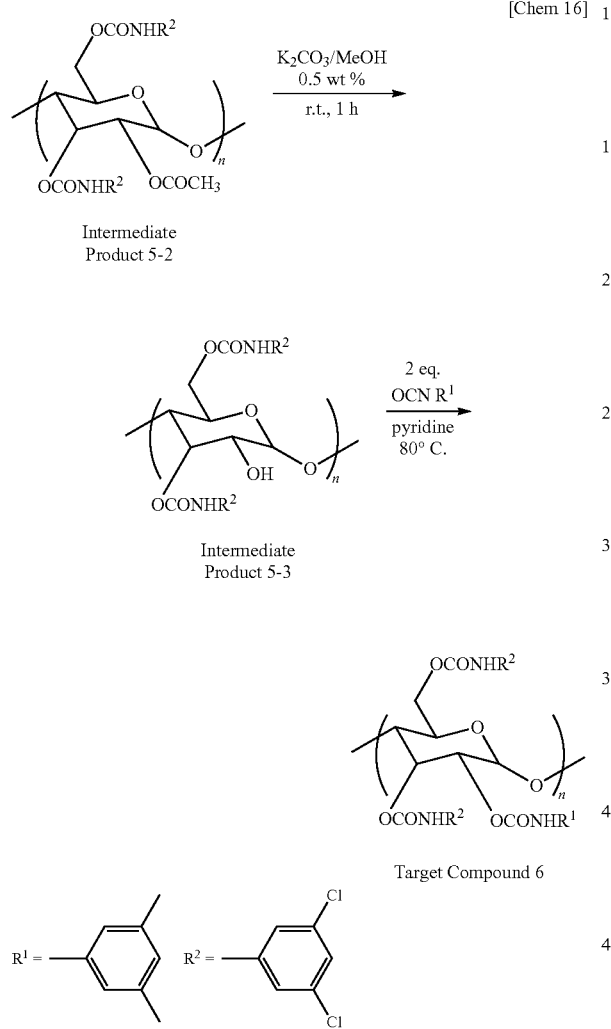

Target Compound 6

Intermediate Product 5-2 was obtained in the same manner as in Synthesis Example 7 except that 3,5-dichlorophenyl isocyanate was used instead of 3,5-dimethylphenyl isocyanate in the synthesis of Intermediate Product 4-2 in Synthesis Example 7. Intermediate Product 5-3 was obtained from Intermediate Product 5-2 thus obtained by hydrolysis (in 82.5% yield) in the same manner as in Synthesis Example 7 except that the concentration of potassium carbonate in the solution of potassium carbonate in methanol was changed to 0.5 mass %. A 0.5-mass % solution of potassium carbonate in methanol was prepared in the same manner as in Synthesis Example 7. 0.3 g (0.56 mmol) of Intermediate Product 5-3 was dissolved in 6 mL of pyridine, and 0.11 mL (1.14 mmol) of 3,5-dimethylphenyl isocyanate was added to the resultant solution. The mixture was subjected to a reaction at 80° C., whereby Target Compound 6 was obtained.

Synthesis Example 10

Synthesis of Target Compound 7 (amylose 2,6-bis(3,5-dimethylphenylcarbamate)-3-(3,5-dichlorophenylcarbamate)

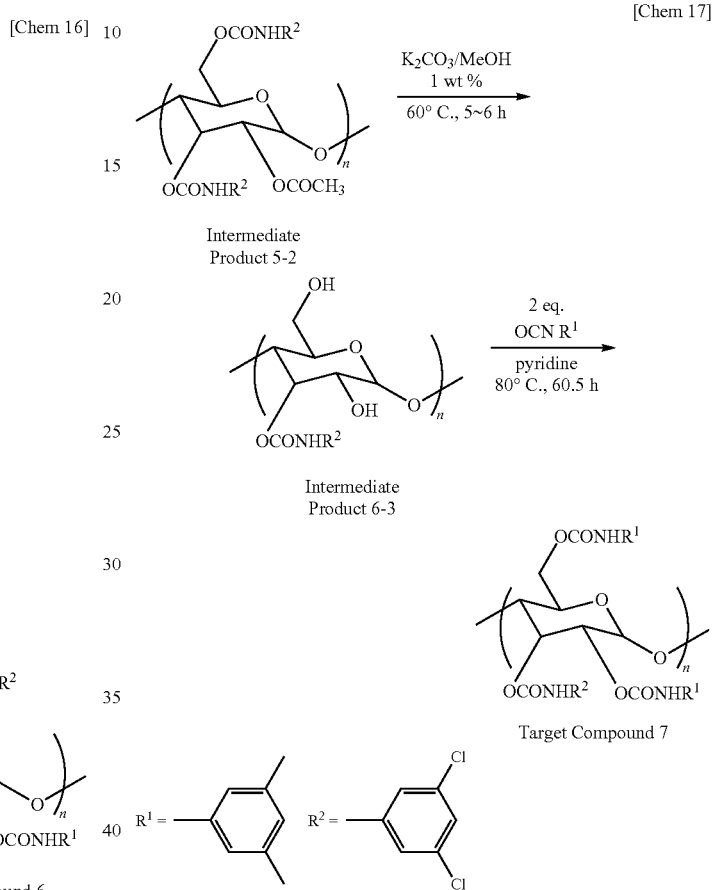

Target Compound 7

Intermediate Product 5-2 was hydrolyzed in the same manner as in Synthesis Example 7 except that: the reaction temperature was changed to 60° C.; and the reaction time was changed to 5 to 6 hours. Thus, Intermediate Product 6-3 obtained by hydrolyzing the 2- and 6-positions of a glucose ring in Intermediate Product 5-2 was obtained. Table 5 shows a yield when the reaction time is changed in the hydrolysis reaction.

TABLE 5

| Usage of Intermediate Product 5-2 | | Usage of pyridine | Composition of base | | Reaction time | Yield |
|---|---|---|---|---|---|---|
| | | | Methanol | Potassium carbonate | | |
| (g) | (mmol) | (mL) | (mL) | (mL) | (hours) | (%) |
| 0.3 | 0.52 | 4.8 | 240 | 24 | 6.0 | 86.7 |
| 0.3 | 0.52 | 4.8 | 240 | 24 | 5.5 | 84.0 |
| 0.3 | 0.52 | 4.8 | 240 | 24 | 5.0 | 81.2 |

Figure 15:
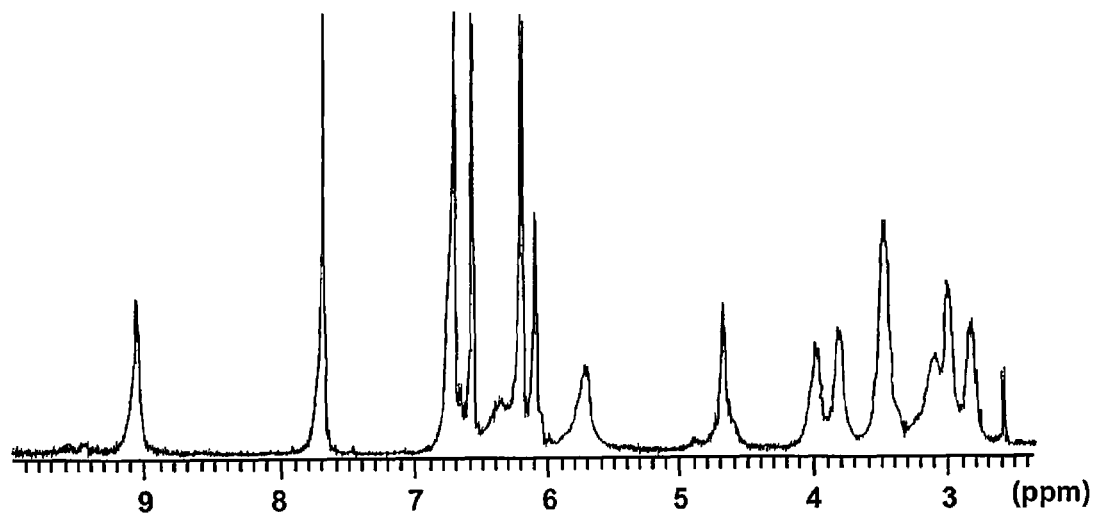
FIG. 15 is a view showing the $^1$H NMR spectrum of Intermediate Product 6-3 obtained in Synthesis Example 10.
Figure 16:
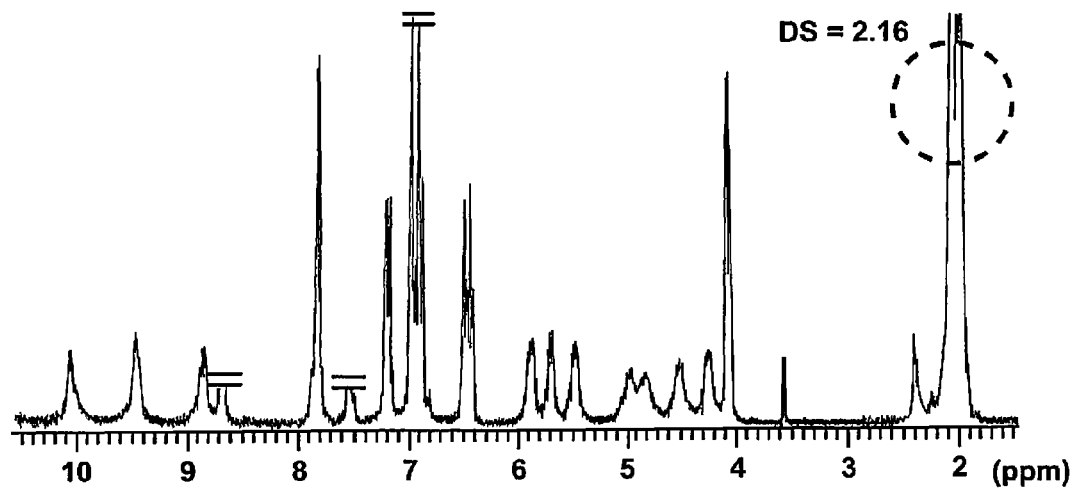
FIG. 16 is a view showing the $^1$H NMR spectrum of Target Compound 7 obtained in Synthesis Example 10.

In addition, FIG. 15 shows the $^1$H NMR spectrum of Intermediate Product 6-3 thus obtained. Next, 0.25 g (0.71 mmol) of Intermediate Product 6-3 purified by reprecipitation was dissolved in 5 mL of pyridine, and 0.27 mL (2.80 mmol) of 3,5-dimethylphenyl isocyanate was added to the solution at room temperature. A container storing the mixture was immersed in an oil bath at 80° C., and then the mixture was subjected to a reaction, whereby Target Compound 7 was obtained (in 98.3% yield). FIG. 16 shows the $^1$H NMR spectrum of Target Compound 7 thus obtained.

Synthesis Example 11

Synthesis of Target Compound 8 (amylose 2-(4-chlorophenylcarbamate)-3-(3,5-dichlorophenylcarbamate)-6-(dimethylphenylcarbamate)

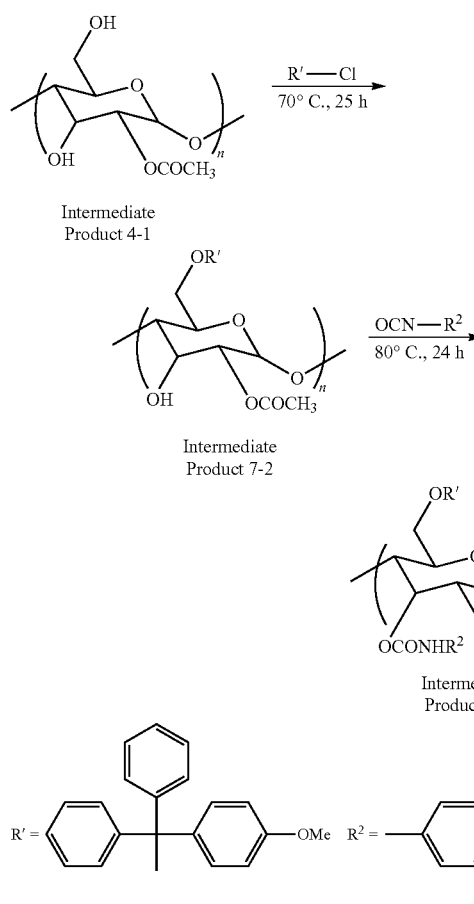

Figure 17:
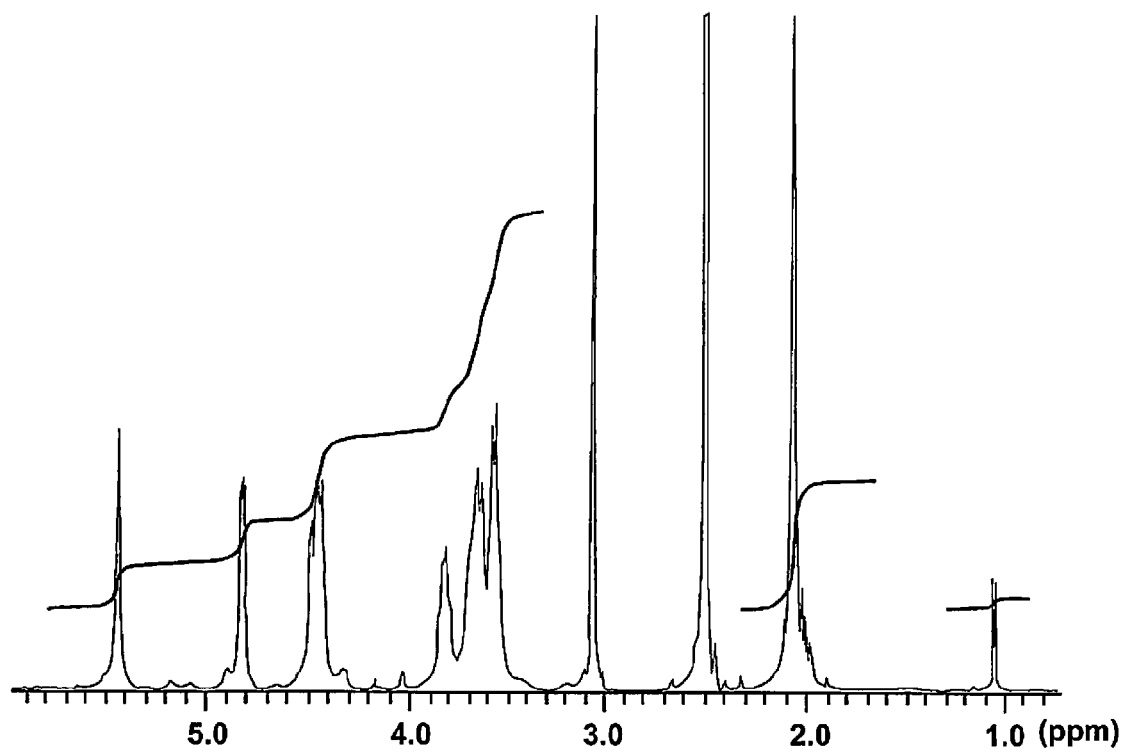
FIG. 17 is a view showing the $^1$H NMR spectrum of Intermediate Product 4-1 obtained in Synthesis Example 11.
Figure 18:
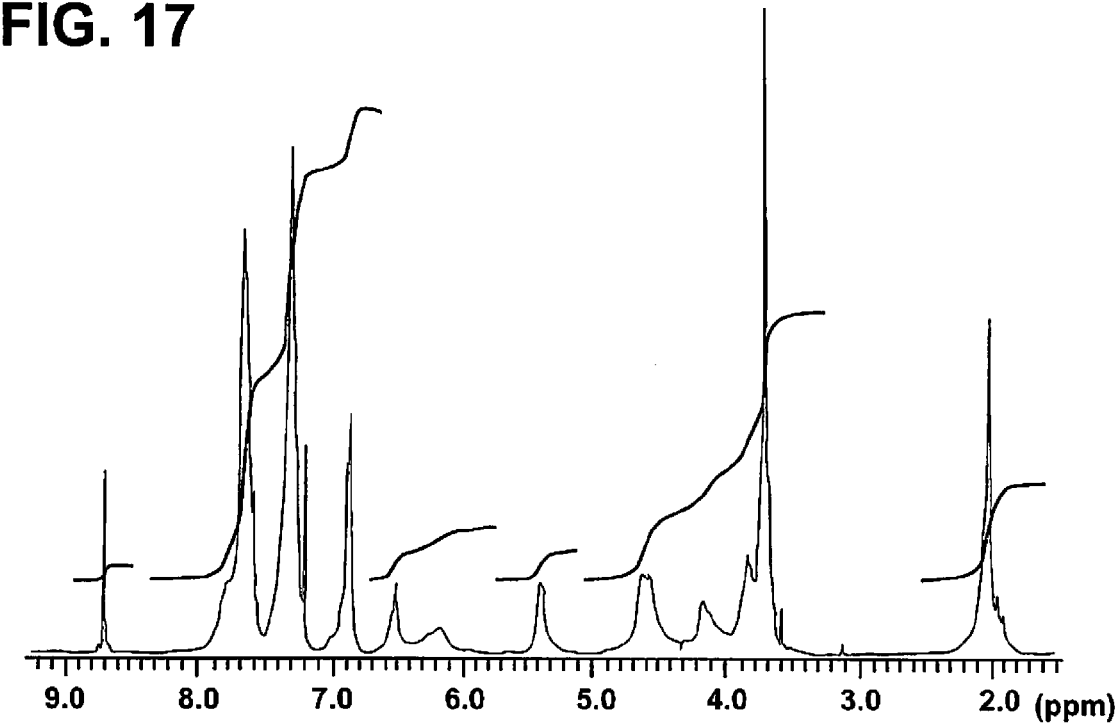
FIG. 18 is a view showing the $^1$H NMR spectrum of Intermediate Product 7-2 obtained in Synthesis Example 11.
Figure 19:
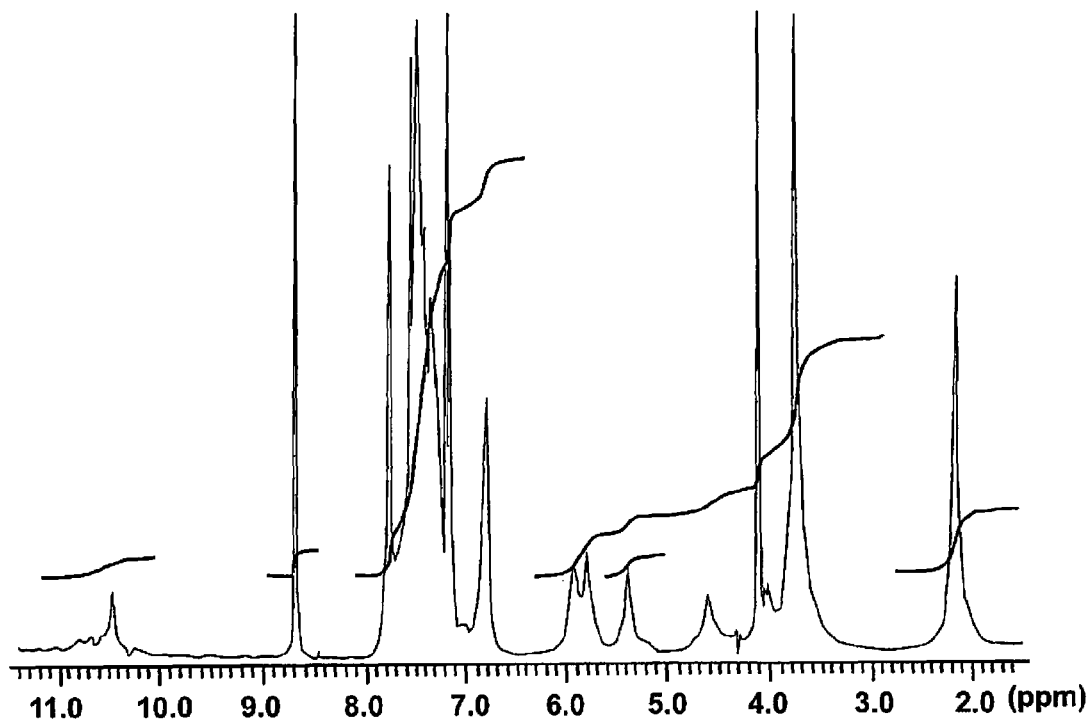
FIG. 19 is a view showing the $^1$H NMR spectrum of Intermediate Product 7-3 obtained in Synthesis Example 11.

1.0 g (4.85 mmol) of Intermediate Product 4-1 was dissolved in 20 mL of pyridine. 4.49 g (14.6 mmol) of 4-methoxytriphenylmethyl chloride were added to the resultant solution, and the mixture was subjected to a reaction at 70° C. for 25 hours. The resultant reaction liquid was poured into 300 mL of methanol, and the resultant precipitate was centrifuged, washed, and dried, whereby 2.63 g of Intermediate Product 7-2 were obtained (in 87.4% yield). Next, 1.50 g (3.14 mmol) of Intermediate Product 7-2 were dissolved in 30 mL of pyridine, and the resultant solution and 0.86 mL (6.31 mmol) of 3,5-dichlorophenyl isocyanate were caused to react with each other at 80° C. for 24 hours. The resultant reaction liquid was poured into 300 mL of methanol, and the precipitate was recovered in the same manner as in Intermediate Product 7-2, whereby 1.78 g of Intermediate Product 7-3 were obtained (in 85.0% yield). FIG. 17 shows the $^1$H NMR spectrum of Intermediate Product 4-1, FIG. 18 shows the $^1$H NMR spectrum of Intermediate Product 7-2 thus obtained, and FIG. 19 shows the $^1$H NMR spectrum of Intermediate Product 7-3.

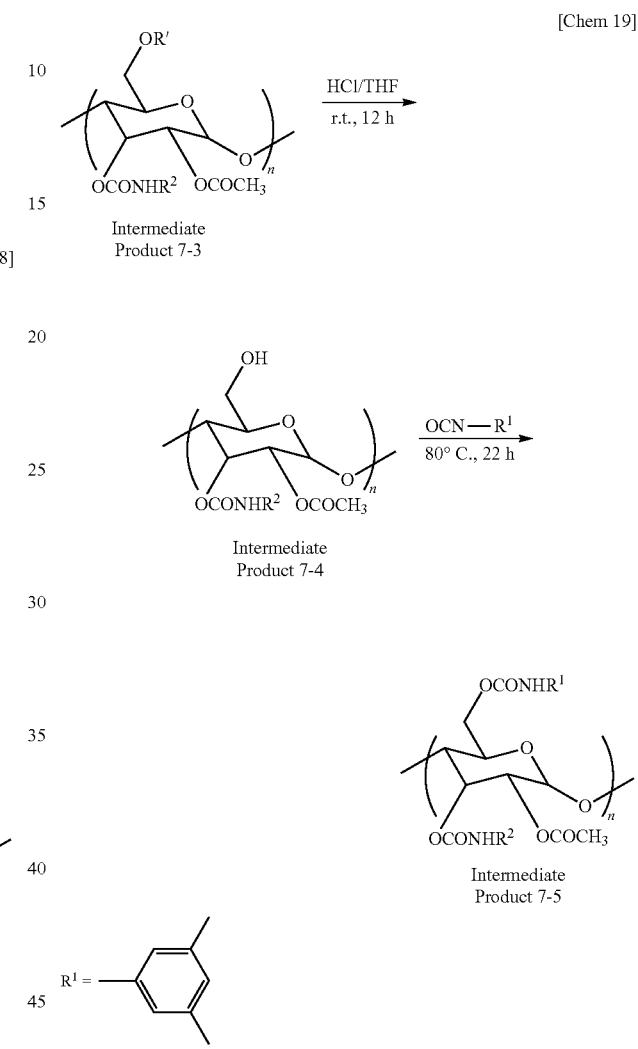

Figure 20:
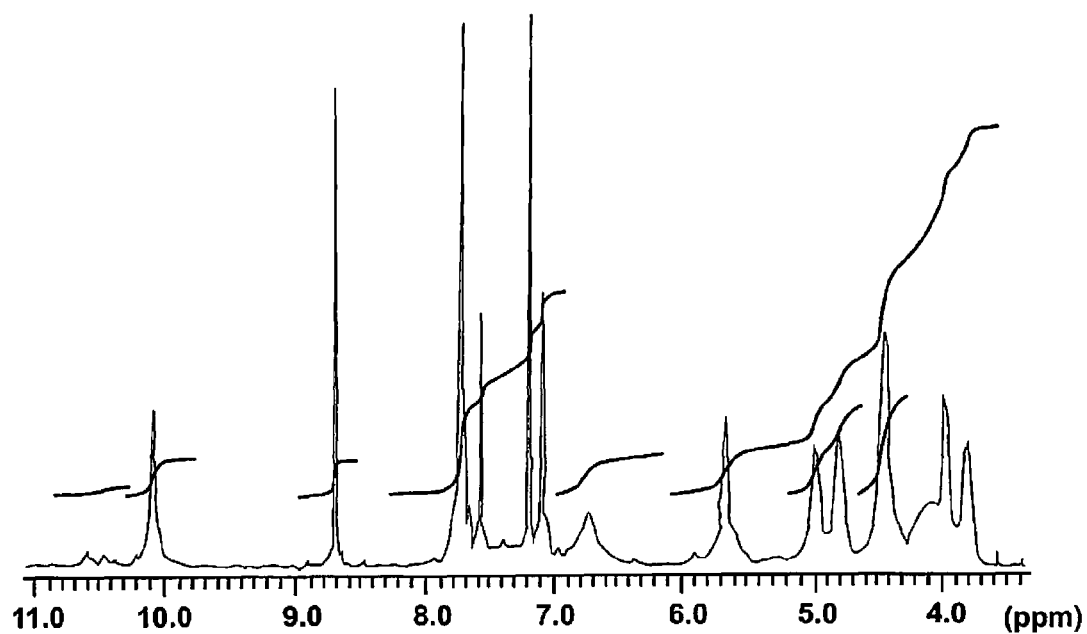
FIG. 20 is a view showing the $^1$H NMR spectrum of Intermediate Product 7-4 obtained in Synthesis Example 11.
Figure 21:
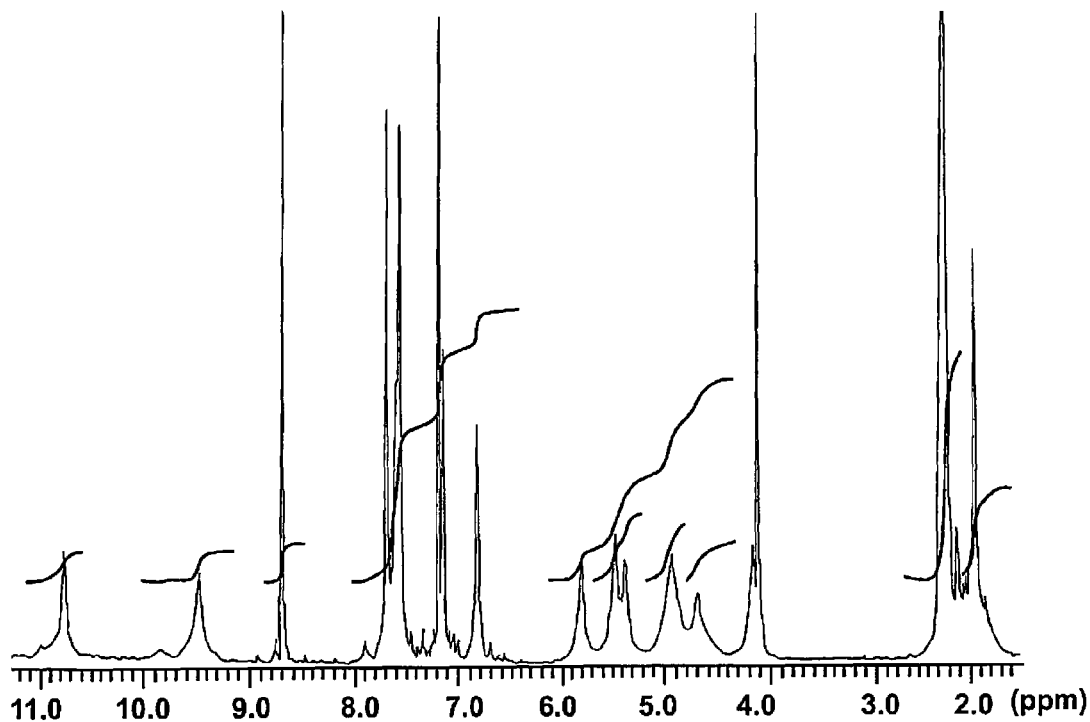
FIG. 21 is a view showing the $^1$H NMR spectrum of Intermediate Product 7-5 obtained in Synthesis Example 11.

1.50 g (2.25 mmol) of Intermediate Product 7-3 were dissolved in 300 mL of THF. 5.6 g of 12N HCl were dropped to the resultant solution, and the mixture was subjected to a reaction at room temperature for 12 hours. The resultant reaction liquid was poured into 700 mL of methanol, and the precipitate was recovered in the same manner as in Intermediate Product 7-2, whereby 0.87 g of Intermediate Product 7-4 was obtained (in 98.4% yield). Next, 0.75 g (1.90 mmol) of Intermediate Product 7-4 was dissolved in 15 mL of pyridine, and the resultant solution and 0.37 mL (3.84 mmol) of 3,5-dimethylphenyl isocyanate were caused to react with each other at 80° C. After the completion of the reaction, the precipitate was recovered in the same manner as in Intermediate Product 7-2, whereby 0.77 g of Intermediate Product 7-5 was obtained (in 74.5% yield). FIG. 20 shows the $^1$H NMR spectrum of Intermediate Product 7-4 thus obtained, and FIG. 21 shows the $^1$H NMR spectrum of Intermediate Product 7-5.

[Chem 20]

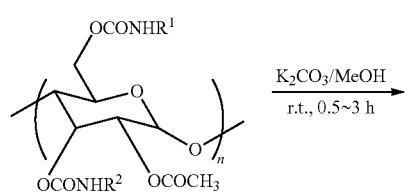

Intermediate
Product 7-5

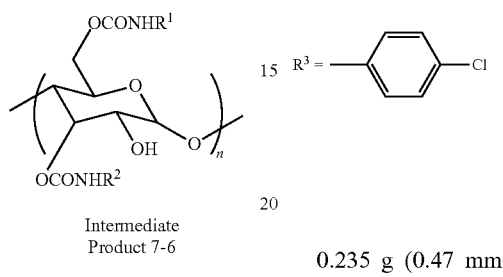

Intermediate
Product 7-6

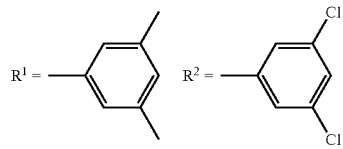

Figure 22:
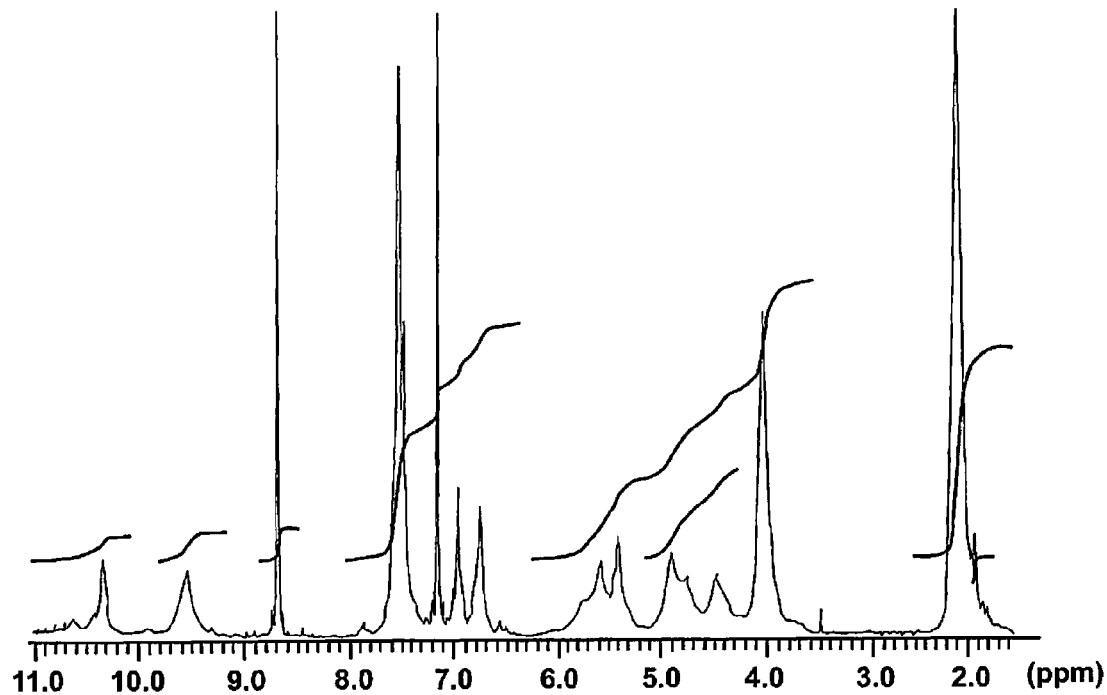
FIG. 22 is a view showing the $^1$H NMR spectrum of Intermediate Product 7-6 obtained in Synthesis Example 11.

0.05 g of Intermediate Product 7-5 was dissolved in 0.8 mL of pyridine. 4 mL of an aqueous solution of potassium carbonate prepared to have a concentration of 10 mass % were charged into 40 mL of methanol, whereby a methanol solution was obtained. The solution of Intermediate Product 7-5 in pyridine was dropped to the methanol solution, and the mixture was subjected to a reaction at room temperature. The resultant was repeatedly subjected to a purifying step by reprecipitation, whereby a total of 0.30 g of Intermediate Product 7-6 was obtained (in 81.6% yield). FIG. 22 shows the $^1$H NMR spectrum of Intermediate Product 7-6 thus obtained.

[Chem 21]

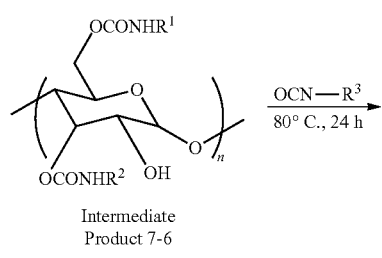

Intermediate
Product 7-6

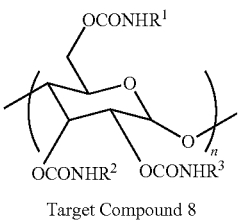

Target Compound 8

$R^3 =$ ⟨4-Cl-phenyl⟩

Figure 23:
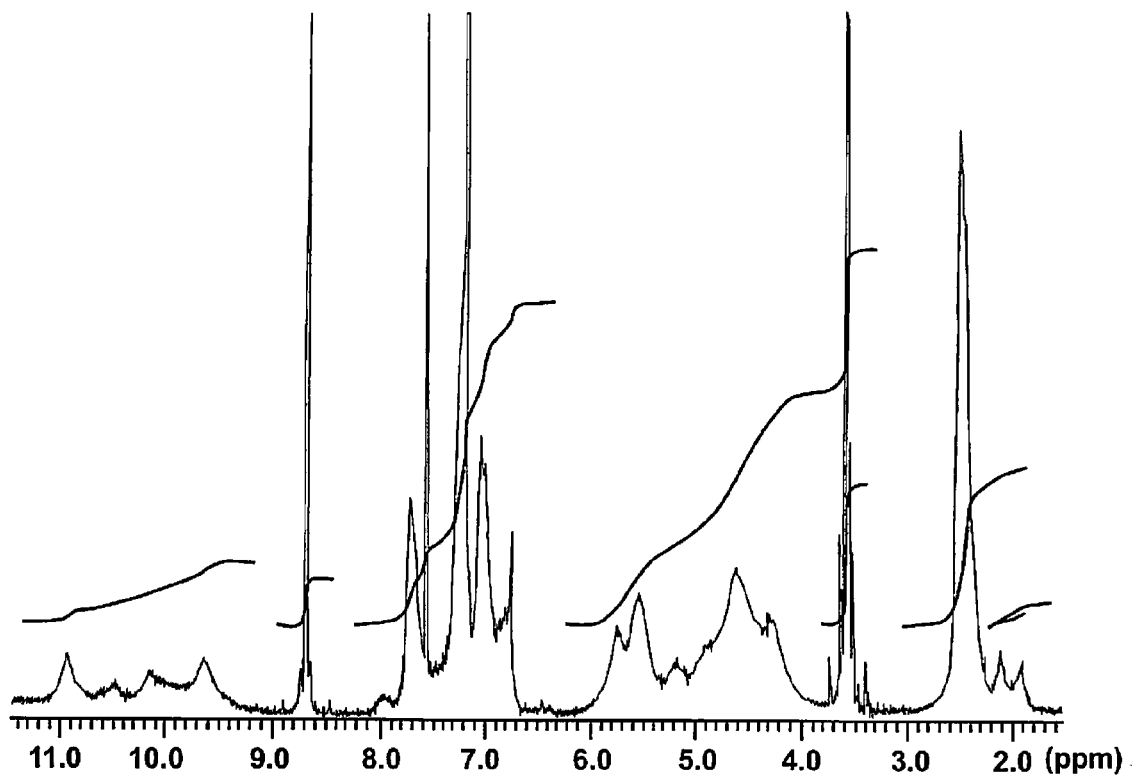
FIG. 23 is a view showing the $^1$H NMR spectrum of Target Compound 8 obtained in Synthesis Example 11.

0.235 g (0.47 mmol) of Intermediate Product 7-6 was dissolved in 4.8 mL of pyridine. 0.12 mL (0.94 mmol) of 4-chlorophenyl isocyanate was added to the resultant solution, and the mixture was subjected to a reaction at 80° C. for 22 hours, whereby Target Compound 8 was obtained. FIG. 23 shows the $^1$H NMR spectrum of Target Compound 8 thus obtained.

[Production of Column for HPLC]

Silica gel the surface of which had been treated was coated with Target Compound 6 as an amylose derivative obtained in Synthesis Example 9, and the resultant silica gel was packed into a column, whereby a column 8 was produced. In addition, silica gel the surface of which had been treated was coated with Target Compound 7 as an amylose derivative obtained in Synthesis Example 10, and the resultant silica gel was packed into a column, whereby a column 9 was produced. Each of those columns was evaluated for its optical resolution on the basis of the optical resolution of the ten kinds of racemic bodies 1 to 10 represented by the foregoing structural formulae. Optical resolution with the column 8 was performed under the separation conditions a, and optical resolution with the column 9 was performed under the separation conditions a. Table 6 shows the position and kind of a substituent in a polysaccharide derivative in each of the columns 8 and 9, and Table 7 shows the results of the evaluation for optical resolution. Table 7 shows the results of columns (the columns 2 and 5) each using a derivative having a benzoate group at any one of its 2-positions as a filler and columns (the columns 6 and 7) each using a filler having the same substituent at its 2-, 3-, and 6-positions as well from the viewpoint of comparison between optical resolutions resulting from differences in the kind and position of a substituent.

TABLE 6

| | Column 7 | Column 5 | Column 8 | Column 6 | Column 2 | Column 9 |
|---|---|---|---|---|---|---|
| 2-position | 3,5-dichloro-phenylcarbamoyl | Benzoyloxy | 3,5-dimethyl-phenylcarbamoyl | 3,5-dimethyl-phenylcarbamoyl | Benzoyloxy | 3,5-dimethyl-phenylcarbamoyl |
| 3-position | 3,5-dichloro-phenylcarbamoyl | 3,5-dichloro-phenylcarbamoyl | 3,5-dichloro-phenylcarbamoyl | 3,5-dimethyl-phenylcarbamoyl | 3,5-dichloro-phenylcarbamoyl | 3,5-dichloro-phenylcarbamoyl |
| 6-position | 3,5-dichloro-phenylcarbamoyl | 3,5-dichloro-phenylcarbamoyl | 3,5-dichloro-phenylcarbamoyl | 3,5-dimethyl-phenylcarbamoyl | 3,5-dimethyl-phenylcarbamoyl | 3,5-dimethyl-phenylcarbamoyl |

TABLE 7

| Racemic body | Column 7 b) | | Column 5 b) | | Column 8 a) | | Column 6 b) | | Column 2 a) | | Column 9 a) | |
|---|---|---|---|---|---|---|---|---|---|---|---|---|
| | $k_1'$ | α | $k_1'$ | α | $k_1'$ | α | $k_1'$ | α | $k_1'$ | α | $k_1'$ | α |
| 1 | 1.26 (−) | ~1 | 4.24 (+) | ~1 | 0.96 (+) | ~1 | 0.61 (−) | ~1 | 3.14 (+) | 1.24 | 0.36 (−) | ~1 |
| 2 | 0.84 (+) | 1.34 | 1.64 (+) | 2.21 | 0.58 (+) | 1.35 | 0.53 (+) | 1.58 | 1.75 (+) | 2.31 | 0.15 (+) | 2.21 |
| 3 | 0.50 (+) | 1.32 | 1.13 (−) | 1.44 | 0.35 (+) | 1.43 | 0.42 (+) | 3.04 | 1.31 (−) | ~1 | 0.11 (+) | 2.62 |
| 4 | 0.88 (+) | 2.25 | 1.53 (+) | 1.34 | 0.85 (+) | 2.75 | 2.65 (+) | 1.98 | 2.01 (+) | 1.22 | 0.72 (+) | 3.36 |
| 5 | 1.10 (+) | ~1 | 3.30 | ~1 | 2.10 (+) | 1.10 | 2.46 (−) | 2.11 | 2.95 (−) | 1.12 | 2.17 (−) | 1.70 |
| 6 | 6.08 (+) | ~1 | 7.48 (−) | 1.89 | 3.56 (−) | 1.14 | 3.14 (−) | 1.21 | 8.45 (−) | 1.97 | 2.02 (−) | 1.38 |
| 7 | 1.62 (+) | 1.10 | 3.53 (−) | 1.20 | 1.23 (+) | 1.26 | 0.93 (+) | 1.12 | 3.60 (+) | 1.13 | 0.51 | 1.00 |
| 8 | 0.63 (+) | ~1 | 1.41 (−) | 1.80 | 0.38 | 1.00 | 0.25 (−) | ~1 | 1.45 (−) | 2.46 | 0.00 | 1.00 |
| 9 | 0.37 | 1.00 | 0.62 | 1.00 | 0.53 | 1.00 | 1.30 (+) | 1.15 | 0.84 (+) | 1.23 | 0.54 (+) | 1.30 |
| 10 | 0.59 (−) | 1.11 | 1.07 (+) | 3.79 | 0.74 (+) | 2.08 | 3.25 (+) | 2.01 | 6.72 (+) | 3.71 | 0.59 (+) | 1.12 |
| α (average) | | 1.21 | | 1.67 | | 1.41 | | 1.62 | | 1.74 | | 1.67 |

In addition, silica gel the surface of which had been treated was coated with Target Compound 8 obtained in Synthesis Example 11 in the same manner as in Target Compound 7 in the production of the column 9, and the resultant silica gel was packed into a column, whereby a column 10 was produced. The column was evaluated for its optical resolution under the separation conditions a on the basis of the optical resolution of the ten kinds of racemic bodies 1 to 10 represented by the foregoing structural formulae. Table 8 shows the position and kind of a substituent in a polysaccharide derivative in the column 10, and Table 9 shows the results of the evaluation for optical resolution. Table 8 shows the columns 2 and 9 as well from the viewpoint of comparison.

TABLE 8

| | Column 2 | Column 9 | Column 10 |
|---|---|---|---|
| 2-position | Benzoyloxy | 3,5-dimethyl-phenylcarbamoyl | 4-chloro-phenylcarbamoyl |
| 3-position | 3,5-dichloro-Phenylcarbamoyl | 3,5-dichloro-phenylcarbamoyl | 3,5-dichloro-phenylcarbamoyl |
| 6-position | 3,5-dimethyl-Phenylcarbamoyl | 3,5-dimethyl-phenylcarbamoyl | 3,5-dimethyl-phenylcarbamoyl |

TABLE 9

| | α | | |
|---|---|---|---|
| Racemic body | Column 2 a) | Column 9 a) | Column 10 a) |
| 1 | 1.24(+) | ~1(−) | ~1(+) |
| 2 | 2.31(+) | 2.21(+) | 1.80(+) |
| 3 | ~1(−) | 2.62(+) | 1.98(+) |
| 4 | 1.22(+) | 3.36(+) | 2.75(+) |
| 5 | 1.12(−) | 1.70(−) | 1.14(−) |
| 6 | 1.97(−) | 1.38(−) | 1.18(−) |
| 7 | 1.13(+) | 1.00 | 1.10(−) |
| 8 | 2.46(−) | 1.00 | 1.00 |
| 9 | 1.23(+) | 1.30(+) | 1.00 |
| 10 | 3.71(+) | 1.12(+) | 1.67(+) |
| α (average) | 1.74 | 1.67 | 1.46 |

As is apparent from Table 9, each of the columns 9 and 10 shows a higher separation factor for each of the racemic bodies 3 to 5 than the column 2 does, and hence each of the columns 9 and 10 has a better optical resolution for each of these racemic bodies than the column 2 does.

INDUSTRIAL APPLICABILITY

When used in a separating agent for optical isomers, the polysaccharide derivative of the present invention shows practicality comparable to or higher than that of an existing separating agent for optical isomers. Further, the separating agent for optical isomers using the polysaccharide derivative shows a higher optical resolution for a certain racemic body as an object to be optically resolved than an existing separating agent for optical isomers does. Therefore, each of the polysaccharide derivative and separating agent for optical isomers of the present invention has a potential to separate optical isomers that have been insufficiently separated with an existing separating agent for optical isomers, and each of the derivative and the agent can be utilized in the development of, for example, a new pharmaceutical in which any such optical isomer is used.

In addition, each of the polysaccharide derivative and separating agent for optical isomers of the present invention may show a higher optical resolution for a certain racemic body as an object to be optically resolved in the case where two kinds of substituents are introduced into the 3- and 6-positions of the polysaccharide of each of the derivative and the separating agent at random than that in the case where these substituents are regularly introduced into the 3- and 6-positions. Therefore, the present invention shows one method of producing a separating agent for optical isomers by which an optical resolution is additionally improved, and the present invention can be utilized in the development of a separating agent for optical isomers having an additionally high optical resolution for a specific optical isomer.

In addition, according to the polysaccharide derivative and separating agent for optical isomers of the present invention, a polysaccharide derivative in which two kinds of similar but non-identical substituents are introduced into the 2- and 3-positions of its polysaccharide may show a higher optical resolution for a certain racemic body as an object to be optically resolved than a polysaccharide derivative in which only one kind of these substituents is introduced into each of both the 2- and 3-positions does. Therefore, the present invention shows another method of producing a separating agent for optical isomers by which an optical resolution is additionally improved, and the present invention can be utilized in the development of a separating agent for optical isomers having an additionally high optical resolution for a specific optical isomer.

What is claimed is:

1. A method of producing a polysaccharide derivative, comprising the steps of (a) or (b):
   (a) modifying a hydroxyl group or amino group at a 2-position of structural units of a polysaccharide with a first substituent represented by a benzoyl group; and
   modifying a hydroxyl group or amino group at a 3-position of the structural units with a second substituent represented by the following general formula (II):

—CO—NH—R  (II), or
   (b) modifying a hydroxyl group or amino group at a 2-position of structural units of a polysaccharide with a first substituent represented by a 4-chlorophenylcarbamoyl group; and
   modifying a hydroxyl group or amino group at a 3-position of the structural units with a second substituent represented by any one of the following general formulae (I) to (III) and different from the first substituent:

—CO—R  (I)

—CO—NH—R  (II)

—R  (III)

wherein R represents an aliphatic or aromatic hydrocarbon group which may contain a heteroatom, and the group may further have a substituent.

2. The method according to claim 1, wherein:
   the structural units each are a hexose further having a hydroxyl group or amino group at its 6-position; and
   the method further comprises the step of protecting the hydroxyl group or amino group at the 6-position with a protective group after modifying the hydroxyl group or amino group at the 2-position.

3. The method according to claim 2, further comprising the steps of:
   removing the protective group at the 6-position after modifying the hydroxyl group or amino group at the 3-position; and
   modifying the hydroxyl group or amino group at the 6-position from which the protective group has been removed with a third substituent represented by any one of the general formulae (I) to (III) and different from the second substituent.

4. A method of producing a polysaccharide derivative, comprising:
   a 2-position protecting step of protecting a hydroxyl group or amino group at a 2-position of structural units of a polysaccharide with a protective group;
   a 3-position modifying step of modifying a hydroxyl group or amino group at a 3-position of the structural units, the 2-position of which has been protected, with a second substituent represented by the following general formula (II) different from the first substituent;
   a 2-position deprotecting step of removing the protective group at the 2-position in the structural units, the 3-position of which has been modified; and
   a 2-position modifying step of modifying the hydroxyl group or amino group at the 2-position from which the protective group has been removed with a first substituent represented by 4-chlorophenylcarbamoyl group:

—CO—NH—R  (II)

wherein R represents an aliphatic or aromatic hydrocarbon group which may contain a heteroatom, and the group may further have a substituent.

5. The method according to claim 4, wherein:
   the structural units each are a hexose further having a hydroxyl group or amino group at its 6-position; and
   the 3-position modifying step is a step of modifying each of the hydroxyl groups or amino groups at both the 3- and 6-positions of the structural units with the second substituent.

6. The method according to claim 5, wherein:
   the 2-position deprotecting step is a step of removing both the protective group at the 2-position and the second substituent at the 6-position; and
   the 2-position modifying step is a step of modifying each of the hydroxyl groups or amino groups at both the 2- and 6-positions of the structural units with the first substituent.

7. The method according to claim 4, wherein:
   the structural units each are a hexose further having a hydroxyl group or amino group at its 6-position;
   the method further comprises
     a 6-position protecting step of protecting the hydroxyl group or amino group at the 6-position of the structural unit, the 2-position of which has been protected, with a protective group before the 3-position modifying step,
     a 6-position deprotecting step of deprotecting the protective group at the 6-position in the structural unit the 3-position of which has been modified in the 3-position modifying step before the 2-position deprotecting step, and
     a 6-position modifying step of modifying the hydroxyl group or amino group at the 6-position from which the protective group has been removed with a third substituent represented by the same general formula as the general formula of each of the first and second substituents but different from the first and second substituents; and
   the 2-position deprotecting step is a step of removing the protective group at the 2-position in the structural unit, the 6-position of which has been modified.

* * * * *